(12) United States Patent
Lee

(10) Patent No.: US 11,647,785 B2
(45) Date of Patent: May 16, 2023

(54) AEROSOL GENERATION DEVICE HAVING STRUCTURE FOR PREVENTING LIQUID LEAKAGE

(71) Applicant: KT&G CORPORATION, Daejeon (KR)

(72) Inventor: Jong Sub Lee, Seongnam-si (KR)

(73) Assignee: KT&G CORPORATION, Daejeon (KR)

( * ) Notice: Subject to any disclaimer, the term of this patent is extended or adjusted under 35 U.S.C. 154(b) by 0 days.

(21) Appl. No.: 16/644,730

(22) PCT Filed: Jun. 14, 2018

(86) PCT No.: PCT/KR2018/006702
§ 371 (c)(1),
(2) Date: Mar. 5, 2020

(87) PCT Pub. No.: WO2019/050131
PCT Pub. Date: Mar. 14, 2019

(65) Prior Publication Data
US 2020/0187555 A1    Jun. 18, 2020

(30) Foreign Application Priority Data

Sep. 6, 2017   (KR) .......................... 10-2017-0113954
Jun. 1, 2018   (KR) .......................... 10-2018-0063759

(51) Int. Cl.
*A24F 13/00*    (2006.01)
*A24F 17/00*    (2006.01)
(Continued)

(52) U.S. Cl.
CPC .............. *A24F 40/20* (2020.01); *A24F 40/40* (2020.01); *A24F 40/46* (2020.01); *A24F 40/60* (2020.01);
(Continued)

(58) Field of Classification Search
CPC .......... A24F 40/20; A24F 40/40; A24F 40/46; A24F 40/60; A24F 40/70
See application file for complete search history.

(56) References Cited

U.S. PATENT DOCUMENTS 2,638,904 A    5/1953 Mitchell
4,585,014 A    4/1986 Fry
(Continued)

FOREIGN PATENT DOCUMENTS

CA    2 973 143 A1    8/2016
CA    2 975 654 A1    8/2016
(Continued)

OTHER PUBLICATIONS

Office Action dated Aug. 7, 2019 in Korean Application No. 10-2018-0067035.
(Continued)

*Primary Examiner* — Abdullah A Riyami
*Assistant Examiner* — Thang H Nguyen
(74) *Attorney, Agent, or Firm* — Sughrue Mion, PLLC

(57) ABSTRACT

An aerosol generation device includes a case into which a cigarette is to be inserted; a protrusion pipe of a hollow shape protruding from one end portion of the case and having an opening; a heater installed in the case such that an end portion thereof is positioned inside the protrusion pipe, and configured to generate heat when an electric signal is applied thereto; and a heater fixing portion installed inside the protrusion pipe to support the heater and comprising a round surface that extends from an inner side surface of the protrusion pipe.

13 Claims, 6 Drawing Sheets

(51) Int. Cl.
  *A24F 25/00* (2006.01)
  *A24F 40/20* (2020.01)
  *A24F 40/46* (2020.01)
  *F16J 15/02* (2006.01)
  *A24F 40/70* (2020.01)
  *A24F 40/40* (2020.01)
  *A24F 40/60* (2020.01)
  *A24D 1/20* (2020.01)

(52) U.S. Cl.
  CPC ............. *A24F 40/70* (2020.01); *F16J 15/021* (2013.01); *A24D 1/20* (2020.01)

(56) References Cited

U.S. PATENT DOCUMENTS

| | | | |
|---|---|---|---|
| 4,637,407 A | 1/1987 | Bonanno et al. | |
| 5,144,962 A | 9/1992 | Counts et al. | |
| 5,240,012 A | 8/1993 | Ehrman et al. | |
| 5,249,586 A | 10/1993 | Morgan et al. | |
| 5,388,594 A | 2/1995 | Counts et al. | |
| 5,465,738 A | 11/1995 | Rowland | |
| 5,479,948 A | 1/1996 | Counts et al. | |
| 5,499,636 A | 3/1996 | Baggett, Jr. et al. | |
| 5,591,368 A | 1/1997 | Fleischhauer et al. | |
| 5,666,977 A | 9/1997 | Higgins et al. | |
| 5,878,752 A * | 3/1999 | Adams .................. | A24F 40/465 131/194 |
| 5,967,148 A | 10/1999 | Harris et al. | |
| 6,026,820 A | 2/2000 | Baggett, Jr. et al. | |
| 6,040,560 A | 3/2000 | Fleischhauer et al. | |
| 6,053,176 A | 4/2000 | Adams et al. | |
| 6,418,938 B1 | 7/2002 | Fleischhauer et al. | |
| 6,532,965 B1 | 3/2003 | Abhulimen et al. | |
| 6,615,840 B1 | 9/2003 | Fournier et al. | |
| 6,810,883 B2 | 11/2004 | Felter et al. | |
| 7,861,726 B1 | 1/2011 | Lukasavitz | |
| 8,375,959 B2 | 2/2013 | Dittrich et al. | |
| 8,419,085 B2 | 4/2013 | Kim et al. | |
| 8,752,545 B2 | 6/2014 | Buchberger | |
| 8,851,081 B2 | 10/2014 | Fernando et al. | |
| 8,973,587 B2 | 3/2015 | Liu | |
| 9,078,472 B2 | 7/2015 | Liu | |
| 9,078,473 B2 | 7/2015 | Worm et al. | |
| 9,220,304 B2 * | 12/2015 | Greim .................. | A24F 40/85 |
| 9,271,528 B2 | 3/2016 | Liu | |
| 9,320,299 B2 | 4/2016 | Hearn et al. | |
| 9,423,152 B2 | 8/2016 | Ampolini et al. | |
| 9,427,023 B2 | 8/2016 | Liu | |
| 9,497,991 B2 | 11/2016 | Besso et al. | |
| 9,499,332 B2 | 11/2016 | Fernando et al. | |
| 9,504,279 B2 | 11/2016 | Chen | |
| 9,516,899 B2 * | 12/2016 | Plojoux .................. | A24F 40/50 |
| 9,560,883 B2 | 2/2017 | Hawes | |
| 9,603,388 B2 * | 3/2017 | Fernando ............... | A24F 40/50 |
| 9,655,383 B2 | 5/2017 | Holzherr et al. | |
| 9,693,587 B2 * | 7/2017 | Plojoux ................ | A61M 15/06 |
| 9,723,871 B2 | 8/2017 | Xiang | |
| 9,795,166 B2 | 10/2017 | Liu | |
| 9,814,263 B2 | 11/2017 | Cochand et al. | |
| 9,844,234 B2 | 12/2017 | Thorens et al. | |
| 9,854,841 B2 | 1/2018 | Ampolini et al. | |
| 9,894,934 B2 | 2/2018 | Li et al. | |
| 9,913,493 B2 * | 3/2018 | Worm .................. | A61M 15/06 |
| 9,918,494 B2 | 3/2018 | Mironov et al. | |
| 9,936,733 B2 * | 4/2018 | Ampolini ................. | H02J 7/00 |
| 9,955,724 B2 | 5/2018 | Lord | |
| 9,986,760 B2 | 6/2018 | Macko et al. | |
| 9,999,247 B2 | 6/2018 | Ruscio et al. | |
| 10,015,990 B2 | 7/2018 | Mironov | |
| 10,031,183 B2 | 7/2018 | Novak, III et al. | |
| 10,070,667 B2 | 9/2018 | Lord et al. | |
| 10,104,911 B2 | 10/2018 | Thorens et al. | |
| 10,130,780 B2 | 11/2018 | Talon | |
| 10,136,673 B2 | 11/2018 | Mironov | |
| 10,159,283 B2 | 12/2018 | Mironov | |
| 10,194,697 B2 | 2/2019 | Fernando et al. | |
| 10,299,513 B2 | 5/2019 | Perez et al. | |
| 10,368,584 B2 | 8/2019 | Fernando et al. | |
| 10,439,419 B2 | 10/2019 | Bernauer et al. | |
| 10,440,987 B2 | 10/2019 | Zeng et al. | |
| 10,448,670 B2 | 10/2019 | Talon et al. | |
| 10,492,542 B1 | 12/2019 | Worm et al. | |
| 10,548,350 B2 * | 2/2020 | Greim .................... | A24F 40/40 |
| 10,555,553 B2 | 2/2020 | Binassi et al. | |
| 10,555,555 B2 | 2/2020 | Fernando et al. | |
| 10,588,351 B2 | 3/2020 | Ricketts | |
| 10,617,149 B2 | 4/2020 | Malgat et al. | |
| 10,631,573 B2 | 4/2020 | Qiu | |
| 10,645,971 B2 | 5/2020 | Zitzke | |
| 10,667,329 B2 | 5/2020 | Bernauer et al. | |
| 10,668,058 B2 | 6/2020 | Rose et al. | |
| 10,716,329 B2 | 7/2020 | Matsumoto et al. | |
| 10,757,975 B2 | 9/2020 | Batista et al. | |
| 10,813,174 B2 | 10/2020 | Schneider et al. | |
| 10,869,499 B2 | 12/2020 | Fernando et al. | |
| 10,869,503 B2 | 12/2020 | Yamada et al. | |
| 10,881,131 B2 | 1/2021 | Matsumoto et al. | |
| 10,881,137 B2 | 1/2021 | Suzuki et al. | |
| 10,881,143 B2 | 1/2021 | Suzuki et al. | |
| 11,039,642 B2 * | 6/2021 | Zuber ...................... | A24D 1/20 |
| 11,147,316 B2 | 10/2021 | Farine et al. | |
| 11,445,576 B2 | 9/2022 | Zinovik et al. | |
| 2004/0261802 A1 * | 12/2004 | Griffin .................... | A24F 40/90 131/194 |
| 2005/0045198 A1 * | 3/2005 | Larson .................... | A24F 40/85 131/194 |
| 2005/0172976 A1 | 8/2005 | Newman et al. | |
| 2006/0030214 A1 | 2/2006 | Katou et al. | |
| 2008/0001052 A1 | 1/2008 | Kalous et al. | |
| 2010/0001538 A1 | 1/2010 | Kim et al. | |
| 2010/0024834 A1 | 2/2010 | Oglesby et al. | |
| 2010/0307518 A1 | 12/2010 | Wang | |
| 2011/0155151 A1 | 6/2011 | Newman et al. | |
| 2011/0226236 A1 | 9/2011 | Buchberger | |
| 2011/0265806 A1 | 11/2011 | Alarcon et al. | |
| 2011/0290248 A1 | 12/2011 | Schennum et al. | |
| 2011/0290269 A1 | 12/2011 | Shimizu | |
| 2012/0048266 A1 | 3/2012 | Alelov | |
| 2012/0247494 A1 | 10/2012 | Oglesby et al. | |
| 2013/0014772 A1 | 1/2013 | Liu | |
| 2013/0037041 A1 | 2/2013 | Worm et al. | |
| 2013/0074857 A1 | 3/2013 | Buchberger | |
| 2013/0213419 A1 | 8/2013 | Tucker et al. | |
| 2013/0284192 A1 | 10/2013 | Peleg et al. | |
| 2013/0319439 A1 | 12/2013 | Gorelick et al. | |
| 2013/0340775 A1 | 12/2013 | Juster et al. | |
| 2014/0014125 A1 | 1/2014 | Fernando et al. | |
| 2014/0020698 A1 | 1/2014 | Fiebelkorn | |
| 2014/0096782 A1 | 4/2014 | Ampolini et al. | |
| 2014/0116455 A1 | 5/2014 | Youn | |
| 2014/0246035 A1 | 9/2014 | Minskoff et al. | |
| 2014/0299137 A1 | 10/2014 | Kieckbusch et al. | |
| 2014/0301721 A1 | 10/2014 | Ruscio et al. | |
| 2014/0318559 A1 | 10/2014 | Thorens et al. | |
| 2014/0345634 A1 | 11/2014 | Zuber et al. | |
| 2014/0363145 A1 | 12/2014 | Plojoux et al. | |
| 2015/0007838 A1 | 1/2015 | Fernando et al. | |
| 2015/0013696 A1 | 1/2015 | Plojoux et al. | |
| 2015/0020832 A1 | 1/2015 | Greim et al. | |
| 2015/0024355 A1 | 1/2015 | Ghofrani et al. | |
| 2015/0027474 A1 | 1/2015 | Zuber et al. | |
| 2015/0100441 A1 | 4/2015 | Alarcon et al. | |
| 2015/0136124 A1 | 5/2015 | Aronie et al. | |
| 2015/0136154 A1 | 5/2015 | Mitrev et al. | |
| 2015/0208725 A1 | 7/2015 | Tsai | |
| 2015/0208730 A1 | 7/2015 | Li et al. | |
| 2015/0245654 A1 * | 9/2015 | Memari .................. | H02J 50/10 141/2 |
| 2015/0245666 A1 | 9/2015 | Memari et al. | |
| 2015/0257445 A1 | 9/2015 | Henry, Jr. et al. | |
| 2015/0272211 A1 | 10/2015 | Chung | |
| 2016/0150824 A1 | 6/2016 | Memari et al. | |
| 2016/0235121 A1 | 8/2016 | Rogan et al. | |

(56) References Cited

U.S. PATENT DOCUMENTS

| | | | |
|---|---|---|---|
| 2016/0270437 A1 | 9/2016 | Nappi | |
| 2016/0270449 A1 | 9/2016 | Hon | |
| 2016/0286861 A1 | 10/2016 | Liu | |
| 2016/0302488 A1 | 10/2016 | Fernando et al. | |
| 2016/0331032 A1 | 11/2016 | Malgat et al. | |
| 2016/0345629 A1 | 12/2016 | Mironov | |
| 2016/0366946 A1 | 12/2016 | Murison et al. | |
| 2017/0006916 A1 | 1/2017 | Liu | |
| 2017/0006919 A1 | 1/2017 | Liu | |
| 2017/0027229 A1 | 2/2017 | Cameron | |
| 2017/0027234 A1 | 2/2017 | Farine et al. | |
| 2017/0042243 A1 | 2/2017 | Plojoux et al. | |
| 2017/0055580 A1 | 3/2017 | Blandino et al. | |
| 2017/0071251 A1 | 3/2017 | Goch | |
| 2017/0095006 A1 | 4/2017 | Egoyants et al. | |
| 2017/0150757 A1 | 6/2017 | Worm et al. | |
| 2017/0164659 A1* | 6/2017 | Schneider | A24F 40/46 |
| 2017/0172214 A1* | 6/2017 | Li | H05B 3/26 |
| 2017/0172215 A1* | 6/2017 | Li | H05B 3/42 |
| 2017/0188634 A1 | 7/2017 | Plojoux et al. | |
| 2017/0295844 A1 | 10/2017 | Thevenaz et al. | |
| 2018/0007962 A1* | 1/2018 | Hunt | B65D 25/38 |
| 2018/0177234 A1 | 6/2018 | Lee | |
| 2018/0206556 A1 | 7/2018 | Thorens et al. | |
| 2018/0235283 A1 | 8/2018 | Zuber et al. | |
| 2019/0014826 A1 | 1/2019 | Thorens et al. | |
| 2019/0075849 A1 | 3/2019 | Hawes | |
| 2019/0320719 A1 | 10/2019 | Liu et al. | |
| 2019/0364975 A1* | 12/2019 | Fernando | H02J 7/007 |
| 2020/0006950 A1 | 1/2020 | Holzherr | |
| 2020/0120983 A1 | 4/2020 | Chen | |
| 2020/0232766 A1 | 7/2020 | Flick | |
| 2020/0305508 A1 | 10/2020 | Talon | |
| 2020/0352224 A1 | 11/2020 | Plojoux et al. | |
| 2020/0413495 A1 | 12/2020 | Schneider et al. | |
| 2021/0000182 A1* | 1/2021 | Ruscio | A24F 40/46 |
| 2021/0120875 A1* | 4/2021 | Mironov | H05B 6/106 |

FOREIGN PATENT DOCUMENTS

| | | |
|---|---|---|
| CH | 310239 A | 12/1955 |
| CN | 2146758 Y | 11/1993 |
| CN | 1102964 A | 5/1995 |
| CN | 1122213 A | 5/1996 |
| CN | 1190335 A | 8/1998 |
| CN | 1209731 A | 3/1999 |
| CN | 2857109 Y | 1/2007 |
| CN | 1973706 A | 6/2007 |
| CN | 101043827 A | 9/2007 |
| CN | 101444335 A | 6/2009 |
| CN | 201491717 U | 6/2010 |
| CN | 102006790 A | 4/2011 |
| CN | 102109393 A | 6/2011 |
| CN | 102326869 A | 1/2012 |
| CN | 102438470 A | 5/2012 |
| CN | 202407082 U | 9/2012 |
| CN | 202774134 U | 3/2013 |
| CN | 103096741 A | 5/2013 |
| CN | 103281920 A | 9/2013 |
| CN | 103338665 A | 10/2013 |
| CN | 103622162 A | 3/2014 |
| CN | 203457802 U | 3/2014 |
| CN | 203575658 U | 5/2014 |
| CN | 103859606 A | 6/2014 |
| CN | 203633505 U | 6/2014 |
| CN | 203646503 U | 6/2014 |
| CN | 103929988 A | 7/2014 |
| CN | 203689071 U | 7/2014 |
| CN | 203692545 U | 7/2014 |
| CN | 103974638 A | 8/2014 |
| CN | 103974640 A | 8/2014 |
| CN | 103987286 A | 8/2014 |
| CN | 103997921 A | 8/2014 |
| CN | 103997922 A | 8/2014 |
| CN | 203789137 U | 8/2014 |
| CN | 104023568 A | 9/2014 |
| CN | 104023574 A | 9/2014 |
| CN | 104039183 A | 9/2014 |
| CN | 203814592 U | 9/2014 |
| CN | 104095295 A | 10/2014 |
| CN | 104106842 A | 10/2014 |
| CN | 203943078 U | 11/2014 |
| CN | 204070570 U | 1/2015 |
| CN | 204146338 U | 2/2015 |
| CN | 102811634 B | 3/2015 |
| CN | 104382237 A | 3/2015 |
| CN | 104470387 A | 3/2015 |
| CN | 104448933 A | 4/2015 |
| CN | 104544559 A | 4/2015 |
| CN | 204317504 U | 5/2015 |
| CN | 104754964 A | 7/2015 |
| CN | 104770878 A | 7/2015 |
| CN | 104799438 A | 7/2015 |
| CN | 104812260 A | 7/2015 |
| CN | 204444239 U | 7/2015 |
| CN | 204763414 U | 11/2015 |
| CN | 105163610 A | 12/2015 |
| CN | 105208882 A | 12/2015 |
| CN | 105208884 A | 12/2015 |
| CN | 105341993 A | 2/2016 |
| CN | 105342011 A | 2/2016 |
| CN | 105357994 A | 2/2016 |
| CN | 205018293 U | 2/2016 |
| CN | 105361250 A | 3/2016 |
| CN | 105453598 A | 3/2016 |
| CN | 205072064 U | 3/2016 |
| CN | 205180371 U | 4/2016 |
| CN | 205197003 U | 5/2016 |
| CN | 205337598 U | 6/2016 |
| CN | 105747281 A | 7/2016 |
| CN | 105789506 A | 7/2016 |
| CN | 105831812 A | 8/2016 |
| CN | 105848503 A | 8/2016 |
| CN | 105876869 A | 8/2016 |
| CN | 205456048 U | 8/2016 |
| CN | 205512358 U | 8/2016 |
| CN | 105939625 A | 9/2016 |
| CN | 205597118 U | 9/2016 |
| CN | 106037014 A | 10/2016 |
| CN | 205648910 U | 10/2016 |
| CN | 106102492 A | 11/2016 |
| CN | 106132217 A | 11/2016 |
| CN | 106163307 A | 11/2016 |
| CN | 205728067 U | 11/2016 |
| CN | 106174699 A | 12/2016 |
| CN | 106231934 A | 12/2016 |
| CN | 205831062 U | 12/2016 |
| CN | 106413439 A | 2/2017 |
| CN | 106413444 A | 2/2017 |
| CN | 106455708 A | 2/2017 |
| CN | 106455714 A | 2/2017 |
| CN | 106455716 A | 2/2017 |
| CN | 106473233 A | 3/2017 |
| CN | 106535680 A | 3/2017 |
| CN | 206097720 U | 4/2017 |
| CN | 106901404 A | 6/2017 |
| CN | 206312988 U | 7/2017 |
| DE | 3302518 A1 | 7/1984 |
| EA | 012169 B1 | 8/2009 |
| EA | 026076 B1 | 2/2017 |
| EP | 1 119 267 B1 | 7/2004 |
| EP | 2 201 850 A1 | 6/2010 |
| EP | 2253233 A1 | 11/2010 |
| EP | 2 022 349 B1 | 7/2014 |
| EP | 2 531 053 B1 | 9/2015 |
| EP | 3 098 738 A1 | 11/2016 |
| EP | 2 432 339 B1 | 3/2017 |
| EP | 3 179 828 A1 | 6/2017 |
| EP | 3 248 485 B1 | 4/2020 |
| EP | 3 275 319 B1 | 8/2020 |
| GB | 2542018 A | 3/2017 |
| GB | 2550540 A | 11/2017 |
| JP | 3-232481 A | 10/1991 |
| JP | 7-184627 A | 7/1995 |

(56) References Cited

FOREIGN PATENT DOCUMENTS

| | | |
|---|---|---|
| JP | 11-40122 A | 2/1999 |
| JP | 11-164679 A | 6/1999 |
| JP | 3645921 B2 | 5/2005 |
| JP | 2006-92831 A | 4/2006 |
| JP | 2006-320286 A | 11/2006 |
| JP | 4278306 B2 | 6/2009 |
| JP | 2010-178730 A | 8/2010 |
| JP | 2010-526553 A | 8/2010 |
| JP | 2011-87569 A | 5/2011 |
| JP | 2011-518567 A | 6/2011 |
| JP | 4739433 B2 | 8/2011 |
| JP | 2012-527222 A | 11/2012 |
| JP | 2014-500017 A | 1/2014 |
| JP | 2014079229 A | 5/2014 |
| JP | 2014-521419 A | 8/2014 |
| JP | 2014-525237 A | 9/2014 |
| JP | 2014-533513 A | 12/2014 |
| JP | 2014-534813 A | 12/2014 |
| JP | 2015-503916 A | 2/2015 |
| JP | 2015-504669 A | 2/2015 |
| JP | 2015-506170 A | 3/2015 |
| JP | 2015-507477 A | 3/2015 |
| JP | 2015-508996 A | 3/2015 |
| JP | 2015-524261 A | 8/2015 |
| JP | 2015-180214 A | 10/2015 |
| JP | 2015-529458 A | 10/2015 |
| JP | 2015-204833 A | 11/2015 |
| JP | 2016-528910 A | 9/2016 |
| JP | 2016-538848 A | 12/2016 |
| JP | 2017-501682 A | 1/2017 |
| JP | 2017-51189 A | 3/2017 |
| JP | 2017-70297 A | 4/2017 |
| JP | 2017-514463 A | 6/2017 |
| KR | 10-0304044 B1 | 11/2001 |
| KR | 10-0806461 B1 | 2/2008 |
| KR | 20-2009-0008911 U | 9/2009 |
| KR | 10-0965099 B1 | 6/2010 |
| KR | 10-1001077 B1 | 12/2010 |
| KR | 10-2011-0096548 A | 8/2011 |
| KR | 20-2011-0009632 U | 10/2011 |
| KR | 10-1098112 B1 | 12/2011 |
| KR | 10-2012-0027029 A | 3/2012 |
| KR | 10-2012-0101637 A | 9/2012 |
| KR | 10-1184499 A | 9/2012 |
| KR | 10-2012-0109634 A | 10/2012 |
| KR | 10-2012-0114333 A | 10/2012 |
| KR | 10-2012-0121314 A | 11/2012 |
| KR | 10-2013-0027909 A | 3/2013 |
| KR | 20-0466757 Y1 | 5/2013 |
| KR | 10-2013-0081238 A | 7/2013 |
| KR | 20-0469513 Y1 | 10/2013 |
| KR | 10-2013-0139296 A | 12/2013 |
| KR | 1020130139298 A | 12/2013 |
| KR | 10-2014-0068203 A | 6/2014 |
| KR | 10-2014-0092312 A | 7/2014 |
| KR | 10-2014-0116055 A | 10/2014 |
| KR | 10-2014-0118983 A | 10/2014 |
| KR | 10-2014-0119072 A | 10/2014 |
| KR | 10-2014-0135774 A | 11/2014 |
| KR | 10-2015-0030409 A | 3/2015 |
| KR | 10-2015-0033617 A | 4/2015 |
| KR | 10-2015-0058569 A | 5/2015 |
| KR | 10-1516304 B1 | 5/2015 |
| KR | 10-1523088 B1 | 5/2015 |
| KR | 10-1523088 B2 | 5/2015 |
| KR | 10-2015-0099771 A | 9/2015 |
| KR | 10-2016-0009678 A | 1/2016 |
| KR | 10-2016-0012110 A | 2/2016 |
| KR | 10-2016-0012329 A | 2/2016 |
| KR | 10-2016-0015144 A | 2/2016 |
| KR | 10-2016-0040643 A | 4/2016 |
| KR | 10-1609715 B1 | 4/2016 |
| KR | 10-2015-0058569 A | 5/2016 |
| KR | 10-2016-0052607 A | 5/2016 |
| KR | 10-1619032 B1 | 5/2016 |
| KR | 20-2016-0001476 U | 5/2016 |
| KR | 10-2016-0060006 A | 6/2016 |
| KR | 10-2016-0088163 A | 7/2016 |
| KR | 10-2016-0094938 A | 8/2016 |
| KR | 10-2016-0096744 A | 8/2016 |
| KR | 10-2016-0108855 A | 9/2016 |
| KR | 10-1656061 B1 | 9/2016 |
| KR | 10-2016-0114743 A | 10/2016 |
| KR | 10-2016-0124091 A | 10/2016 |
| KR | 10-1667124 B1 | 10/2016 |
| KR | 10-1668175 B1 | 10/2016 |
| KR | 10-2016-0129024 A | 11/2016 |
| KR | 10-2016-0131035 A | 11/2016 |
| KR | 10-2016-0133665 A | 11/2016 |
| KR | 10-2016-0137627 A | 11/2016 |
| KR | 10-1679489 B1 | 11/2016 |
| KR | 10-2016-0140608 A | 12/2016 |
| KR | 10-2016-0142896 A | 12/2016 |
| KR | 10-2016-0147253 A | 12/2016 |
| KR | 10-1690389 B1 | 12/2016 |
| KR | 10-2017-0006282 A | 1/2017 |
| KR | 10-2017-0007262 A | 1/2017 |
| KR | 10-2017-0044158 A | 4/2017 |
| KR | 10-2017-0071486 A | 6/2017 |
| KR | 10-2017-0074898 A | 6/2017 |
| KR | 10-1740160 B1 | 6/2017 |
| KR | 1020180018794 A | 2/2018 |
| RU | 2302806 C2 | 7/2007 |
| RU | 2425608 C2 | 8/2011 |
| RU | 2 531 890 C2 | 10/2014 |
| RU | 2564600 C1 | 10/2015 |
| RU | 2014 125 232 A | 12/2015 |
| RU | 2581999 C2 | 4/2016 |
| RU | 2589437 C2 | 7/2016 |
| RU | 2594557 C2 | 8/2016 |
| RU | 2595593 C2 | 8/2016 |
| RU | 2 602 053 C2 | 11/2016 |
| RU | 2 602 962 C2 | 11/2016 |
| RU | 2 603 559 C2 | 11/2016 |
| RU | 2 604 012 C2 | 12/2016 |
| RU | 2604012 C2 | 12/2016 |
| UA | 104628 C2 | 2/2014 |
| WO | 94/06314 A1 | 3/1994 |
| WO | 98/23171 A1 | 6/1998 |
| WO | 00/27232 A1 | 5/2000 |
| WO | 2010/133342 A1 | 11/2010 |
| WO | 2011/028372 A1 | 3/2011 |
| WO | 2011/095781 A1 | 8/2011 |
| WO | 2012/072264 A1 | 6/2012 |
| WO | 2012/123702 A1 | 9/2012 |
| WO | 2013/034458 A1 | 3/2013 |
| WO | 2013/060743 A2 | 5/2013 |
| WO | 2013/076098 A1 | 5/2013 |
| WO | 2013/098395 A1 | 7/2013 |
| WO | 2013/098398 A3 | 7/2013 |
| WO | 2013/098409 A1 | 7/2013 |
| WO | 2013/102609 A2 | 7/2013 |
| WO | 2013/102612 A2 | 7/2013 |
| WO | 2013102609 A2 | 7/2013 |
| WO | 2013/120565 A3 | 8/2013 |
| WO | 2013/126777 A2 | 8/2013 |
| WO | 2013/137084 A1 | 9/2013 |
| WO | 2013/171217 A1 | 11/2013 |
| WO | 2014/029880 A2 | 2/2014 |
| WO | 2015/046386 A1 | 4/2015 |
| WO | 2015/088744 A1 | 6/2015 |
| WO | 2015088744 A1 | 6/2015 |
| WO | 2015/128665 A1 | 9/2015 |
| WO | 2015128665 A1 | 9/2015 |
| WO | 2015/155289 A1 | 10/2015 |
| WO | 2015/165813 A1 | 11/2015 |
| WO | 2015/174657 A1 | 11/2015 |
| WO | 2015/177044 A1 | 11/2015 |
| WO | 2015/197627 A1 | 12/2015 |
| WO | 2016/059073 A1 | 4/2016 |
| WO | 2016/075028 A1 | 5/2016 |
| WO | 2016/076147 A1 | 5/2016 |
| WO | 2016075028 A1 | 5/2016 |
| WO | 2016/107766 A1 | 7/2016 |

(56) References Cited

FOREIGN PATENT DOCUMENTS

| WO | 2016/124550 A1 | 8/2016 |
|---|---|---|
| WO | 2016/124552 A1 | 8/2016 |
| WO | 2016/150019 A1 | 9/2016 |
| WO | 2016/156103 A1 | 10/2016 |
| WO | 2016/156219 A1 | 10/2016 |
| WO | 2016/159013 A1 | 10/2016 |
| WO | 2016166064 A1 | 10/2016 |
| WO | 2016178377 A1 | 11/2016 |
| WO | 2016187803 A1 | 12/2016 |
| WO | 2017/029088 A1 | 2/2017 |
| WO | 2017/029089 A1 | 2/2017 |
| WO | 2017/037457 A1 | 3/2017 |
| WO | 2017/042297 A1 | 3/2017 |
| WO | 2017/075759 A1 | 5/2017 |
| WO | 2017/139963 A1 | 8/2017 |
| WO | 2018/050449 A1 | 3/2018 |
| WO | 2018/189195 A1 | 10/2018 |
| WO | 2019/020826 A1 | 1/2019 |
| WO | 2019/030172 A1 | 2/2019 |
| WO | 2019/095268 A1 | 5/2019 |

OTHER PUBLICATIONS

Office Action dated Jun. 27, 2019 in Korean Application No. 10-2018-0063759.
Office Action dated Jun. 19, 2019 in Korean Application No. 10-2018-0059279.
Office Action dated Feb. 7, 2020 in Korean Application No. 10-2017-0146697.
International Search Report dated Dec. 4, 2018 in International Application No. PCT/KR2018/006747.
International Search Report dated Nov. 30, 2018 in International Application No. PCT/KR2018/006702.
International Search Report dated Aug. 29, 2018 in International Application No. PCT/KR2018/005945.
International Search Report dated May 29, 2018 in International Application No. PCT/KR2017/012486.
Partial supplementary European search report dated Aug. 3, 2020 in Application No. 17880867.1.
Extended European search report dated Nov. 4, 2020 by the European Patent Office in Application No. 17880867.1.
Office Action dated Oct. 29, 2020 by the Korean Patent Office in Application No. 10-2018-0010837.
Office Action dated Nov. 4, 2020 by the Japanese Patent Office in Application No. 2019-554453.
Office Action dated Nov. 4, 2020 by the Japanese Patent Office in Application No. 2020-128346.
Decision on Grant dated Nov. 26, 2020 by the Russian Federal Service For Intellectual Property Patent Application No. 2020124607.
Office Action dated Nov. 26, 2020 by Russian Federal Service For Intellectual Property Office Patent Application No. 2020124609.
Decision on Grant dated Oct. 26, 2020 by Russian Federal Service For Intellectual Property in Application No. 2020124610.
Office Action dated Jun. 29, 2020 by the Korean Patent Office in Application No. 10-2018-0010836.
Extended European Search Report dated Dec. 11, 2020 in European Application No. 20188967.2.
Extended European Search Report dated Jan. 15, 2021 in European Application No. 20188949.0.
Extended European Search Report dated Dec. 16, 2020 in European Application No. 20188985.4.
Office Action dated Dec. 30, 2020 in Russian Application No. 2020124651.
Office Action dated Dec. 28, 2020 in Russian Application No. 2020124652.
Office Action dated Dec. 11, 2020 in Russian Application No. 2020124653.
Office Action dated Jan. 22, 2021 in Russian Application No. 2020124657.
Office Action dated Jan. 22, 2021 in Russian Application No. 2020124658.
Extended European Search Report dated Dec. 18, 2020 in European Application No. 18775504.6.
Office Action dated Jan. 19, 2021 in Japanese Application No. 2019-553569.
Extended European Search Report dated Jan. 14, 2021 in European Application No. 18784738.9.
Extended European Search Report dated Dec. 10, 2020 in European Application No. 20188932.6.
Office Action dated Jan. 12, 2021 in Japanese Application No. 2019-555201.
Office Action dated Jan. 12, 2021 in Japanese Application No. 2019-555169.
Office Action dated Jan. 5, 2021 in Japanese Application No. 2019-558557.
Extended European Search Report dated Nov. 19, 2020 in European Application No. 20188792.4.
Office Action dated Dec. 1, 2020 in Japanese Application No. 2020-501188.
Extended European Search Report dated Dec. 18, 2020 in European Application No. 20188926.8.
Office Action dated Jan. 19, 2021 in Japanese Application No. 2020-501514.
Office Action dated Sep. 24, 2020 in Korean Application No. 10-2018-0012456.
Office Action dated May 28, 2020 in Korean Application No. 10-2017-0147605.
Extended European Search Report dated Jan. 14, 2021 in European Application No. 18783776.0.
Extended European Search Report dated Jan. 25, 2021 in European Application No. 18785166.2.
Extended European Search Report dated Jan. 29, 2021 in European Application No. 18784464.2.
Extended European Search Report dated Mar. 15, 2021 in European Application No. 18785061.5.
Extended European Search Report dated Mar. 19, 2021 in European Application No. 18784164.8.
Extended European Search Report dated Mar. 24, 2021 in European Application No. 18784268.7.
Extended European Search Report dated Mar. 25, 2021 in European Application No. 18784370.1.
Extended European Search Report dated Mar. 25, 2021 in European Application No. 18784841.1.
Office Action dated Feb. 24, 2021 in Japanese Application No. 2019-555168.
Office Action dated Feb. 24, 2021 in Japanese Application No. 2019-555203.
Office Action dated Feb. 24, 2021 in Japanese Application No. 2019-555204.
Office Action dated Feb. 4, 2021 in Russian Application No. 2020124609.
Office Action dated Feb. 9, 2021 in Japanese Application No. 2019-555184.
Office Action dated Jan. 26, 2021 in Japanese Application No. 2020-501521.
Office Action dated Mar. 2, 2021 in Japanese Application No. 2019-555170.
Office Action dated Mar. 2, 2021 in Japanese Application No. 2019-555182.
Office Action dated Mar. 30, 2021 in Japanese Application No. 2020-501377.
Office Action dated Jan. 19, 2021 in Indonesian Application No. P00201906007.
Communication dated Jul. 22, 2021 by the Korean Patent Office in Korean Application No. 10-2021-0051359.
Communication dated Jul. 27, 2021 by the Chinese Patent Office in Chinese Application No. 201780084891.5.
Communication dated Aug. 16, 2021 by the Chinese Patent Office in Chinese Application No. 201880024006.9.
Communication dated Aug. 26, 2021 by the Chinese Patent Office in Chinese Application No. 201880024107.6.

(56) References Cited

OTHER PUBLICATIONS

Communication dated Aug. 4, 2021 by the Chinese Patent Office in Chinese Application No. 201880024289.7.
Communication dated Jul. 26, 2021 by the Chinese Patent Office in Chinese Application No. 201880024059.0.
Communication dated Jul. 16, 2021 by the Chinese Patent Office in Chinese Application No. 201880024367.3.
Communication dated Jul. 19, 2021 by the Chinese Patent Office in Chinese Application No. 201880024070.7.
Communication dated Sep. 17, 2021 by the Chinese Patent Office in Chinese Application No. 201880030699.2.
Communication dated Apr. 2, 2019, issued by the Korean Intellectual Property Office in application No. 10-2019-0021286.
Communication dated Apr. 3, 2019, issued by the Korean Intellectual Property Office in application No. 10-2019-0018812.
Communication dated Apr. 4, 2019, issued by the Korean Intellectual Property Office in application No. 10-2019-0020484.
Communication dated Apr. 4, 2019, issued by the Korean Intellectual Property Office in application No. 10-2019-0019194.
Communication dated Apr. 4, 2019, issued by the Korean Intellectual Property Office in application No. 10-2019-0019195.
Communication dated Apr. 5, 2019, issued by the Korean Intellectual Property Office in application No. 10-2019-0027638.
Communication dated Apr. 25, 2019, issued by the Korean Intellectual Property Office in application No. 10-2019-0033721.
Communication dated Apr. 25, 2019, issued by the Korean Intellectual Property Office in application No. 10-2019-0033784.
Communication dated Apr. 9, 2021, issued by the Korean Intellectual Property Office in application No. 10-2020-0116256.
Communication dated May 5, 2021, issued by the Canadian Patent Office in application No. 3,047,236.
Extended European Search Report dated Jan. 15, 2021, issued by the European Patent Office in application No. 20188949.0.
Communication dated Feb. 18, 2020, issued by the Russian Patent Office in application No. 2019121813/12.
Communication dated Jun. 29, 2021, issued by the State Intellectual Property Office of the P.R.C. in application No. 201880022072.2.
Extended European Search Report dated Apr. 1, 2021, issued by the European Patent Office in application No. 18805933.1.
Extended European Search Report dated Jun. 16, 2021, issued by the European Patent Office in application No. 18853434.1.
Extended European Search Report dated Jul. 1, 2021, issued by the European Patent Office in application No. 18854661.8.
Extended European Search Report dated Jun. 14, 2021, issued by the European Patent Office in application No. 18842951.8.
International Search Report dated Jul. 24, 2018, issued by the International Searching Authority in application No. PCT/KR2018/003691.
International Search Report dated Sep. 6, 2018, issued by the International Searching Authority in application No. PCT/KR2018/004176.
International Search Report dated Nov. 14, 2018, issued by the International Searching Authority in application No. PCT/KR2018/004118.
International Search Report dated Nov 6, 2018, issued by the International Searching Authority in application No. PCT/KR2018/004178.
International Search Report dated Sep. 7, 2018, issued by the International Searching Authority in application No. PCT/KR2018/004171.
International Search Report dated Sep. 7, 2018, issued by the International Searching Authority in application No. PCT/KR2018/004172.
International Search Report dated Nov. 6, 2018, issued by the International Searching Authority in application No. PCT/KR2018/004129.
International Search Report dated Nov. 6, 2018, issued by the International Searching Authority in application No. PCT/KR2018/004130.
International Search Report dated Sep. 6, 2018, issued by the International Searching Authority in application No. PCT/KR2018/004179.
International Search Report dated Nov. 26, 2018, issued by the International Searching Authority in application No. PCT/KR2018/009094.
International Search Report dated Feb. 28, 2019, issued by the International Searching Authority in application No. PCT/KR2018/009100.
Extended European Search Report dated Oct. 27, 2021 in European Application No. 18844735.3.
Office Action dated Oct. 28, 2021 in Chinese Application No. 201880046418.2.
Office Action dated Sep. 24, 2021 in Chinese Application No. 201880024010.5.
Office Action dated Sep. 29, 2021 in Chinese Application No. 201880024276.X.
Office Action dated Sep. 29, 2021 in Chinese Application No. 201880024311.8.
Office Action dated Nov. 25, 2021 in Chinese Application No. 201880047174.X.
Office Action dated Dec. 1, 2021 in Chinese Application No. 201880046367.3.
Communication dated Mar. 14, 2022 from the Chinese Patent Office in Chinese Application No. 201880024059.0.
Communication dated Feb. 28, 2022 from the Chinese Patent Office in Chinese Application No. 201880050526.7.
Communication dated May 30, 2022 from the Canadian Intellectual Property Office in Application No. 3080145.
Communication dated Jun. 9, 2022 from the Intellectual Property Office of the Philippines in Application No. 12019501361.
Notice of Reasons for Refusal issued in the Japanese Patent Office dated Jun. 28, 2022 in corresponding Japanese Patent Application No. 2021-075028.
Third Office Action issued in the China National Intellectual Property Administration dated Aug. 12, 2022 in corresponding Chinese Application No. 201880024059.0.
Notice of Reasons for Refusal issued in the Japanese Patent Office dated Sep. 20, 2022 in corresponding Japanese Patent Application No. 2021-174035.
Office Action dated Nov. 2, 2022 in Chinese Application No. 201880050526.7.
Office Action dated Nov. 22, 2022 in Chinese Application No. 202010762996.5.
Office Action dated Oct. 24, 2022 in Ukranian Application No. a 2020 014868.
Office Action dated Oct. 27, 2022 in Ukranian Application No. a 2020 04869.
Notice of Reasons for Refusal issued in the Japanese Patent Office in corresponding Japanese Patent Application No. 2021-165298 dated Dec. 13, 2022.
First Office Action issued in the China National Intellectual Property Administration dated Dec. 30, 2022 in corresponding Chinese Patent Application No. 202010756239.7.
Notice of Reasons for Refusal dated Jan. 10, 2023 in the Japanese Patent Office in corresponding Japanese Patent Application No. 2021-177649.
First Office Action dated Jan. 3, 2023 in the China National Intellectual Property Administration in corresponding Chinese Patent Application No. 202010760979.8.
First Office Action issued in the China National Intellectual Property Administration dated Jan. 10, 2023 in corresponding Chinese Patent Application No. 202010760990.4.
First Office Action issued in the China National Intellectual Property Administration dated Jan. 28, 2023 in corresponding Chinese Patent Application No. 202010763214.X.

\* cited by examiner

AEROSOL GENERATION DEVICE HAVING STRUCTURE FOR PREVENTING LIQUID LEAKAGE

TECHNICAL FIELD

The present disclosure relates to an aerosol generation device, and more particularly, to a non-combustion aerosol generation device.

BACKGROUND ART

Recently, there has been a growing demand for alternative methods for resolving the problems of common cigarettes. For example, there is a growing demand for a method of generating aerosols by heating an aerosol generating material in a cigarette instead of burning the cigarette to generate aerosols. Therefore, research into non-combustion aerosol generation devices such as heating-type cigarettes or heating-type aerosol generation devices has been actively carried out.

A non-combustion aerosol generation device refers to a device that generates an aerosol from an aerosol generation material included in a cigarette by heating the cigarette at a predetermined temperature without combusting the cigarette so that the aerosol can be inhaled with air.

An entire amount of the aerosol generated from the cigarette is preferably delivered to a user, but in an air passage provided inside the non-combustion aerosol generation device, water or the aerosol is partially liquefied and fixed in the form of droplets, and the leakage of liquid penetrates the inside of the device, which may cause failure or malfunction of the device.

The above-mentioned background art is technical information possessed by the inventors for the derivation of the exemplary embodiments of the present disclosure or acquired in a derivation process, and may not be necessarily referred to as publicly known technology disclosed to the general public before the application of the exemplary embodiments of the present disclosure.

DESCRIPTION OF EXEMPLARY EMBODIMENTS

Technical Problem

Provided is an aerosol generation device having a structure to prevent a liquid material liquefied by passing through an internal air passage from penetrating into the device.

Provided are aerosol generation device and method capable of providing a user with a variety of experiences and ease of use by using a combination of an aerosol generation source and a cigarette.

In addition, provided is an aerosol including abundant flavor, nicotine, etc. by passing, through a cigarette, an aerosol generated by heating an aerosol generation source.

Solution to Problem

According to an exemplary embodiment of the present disclosure, an aerosol generation device includes a case into which a cigarette may be inserted; a protrusion pipe of a hollow shape protruding from one end portion of the case and open toward an outside; a heater installed at the case such that an end portion is positioned inside the protrusion pipe and configured to generate heat when an electric signal is applied; and a heater fixing portion in contact with the protrusion pipe and installed inside the case to support the heater.

Advantageous Effects of Disclosure

The aerosol generation device according to the exemplary embodiments of the present disclosure as described above may include a round surface that leads a liquid material liquefied by passing through an internal air passage, toward a heater, thereby preventing the liquid material from penetrating into the device.

In addition, the aerosol generation device may include a heater fixing portion that serves as a breakwater that collects a liquid material liquefied by passing through an internal air passage, thereby preventing the liquid material from penetrating into the device.

In addition, the aerosol generation device may include a sealing member that seals a passage installed in the passage through which a liquid material liquefied by passing through an internal air passage penetrates into the device, thereby preventing the liquid material from penetrating into the device.

In addition, the aerosol generation device may generate an aerosol from an aerosol generation source and then allow a flow of the generated aerosol to pass through a cigarette, thereby providing the aerosol including a flavor and nicotine suitable for the user.

BEST MODE

Figure 1:
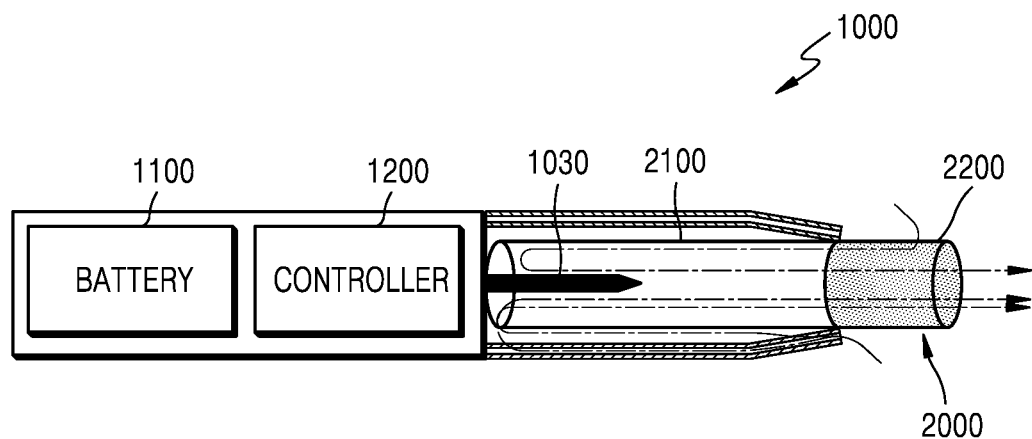
FIG. 1 is a drawing illustrating an exemplary embodiment in which a cigarette is inserted into an aerosol generation device.

According to an exemplary embodiment of the present disclosure, an aerosol generation device includes a case into which a cigarette is to be inserted; a protrusion pipe of a hollow shape protruding from one end portion of the case and having an opening; a heater installed in the case such that an end portion thereof is positioned inside the protrusion pipe, and configured to generate heat when an electric signal is applied thereto; and a heater fixing portion installed inside the protrusion pipe to support the heater, and comprising a round surface that extends from an inner side surface of the protrusion pipe.

The aerosol generation device may further include a sealing member interposed between the protrusion pipe and the heater fixing portion to seal a gap between the protrusion pipe and the heater fixing portion.

The heater fixing portion may further include a sealing groove formed to be drawn in from a surface in contact with the protrusion pipe, and the sealing member may be installed in the sealing groove.

The protrusion pipe may include a sealing groove formed to be drawn in from a surface in contact with the heater fixing portion, and the sealing member may be installed in the sealing groove.

The sealing member may include an elastic material.

According to another exemplary embodiment of the present disclosure, an aerosol generation device includes a case into which a cigarette may be inserted; a protrusion pipe of a hollow shape protruding from one end portion of the case and having an opening; a heater installed at the case such that an end portion is positioned inside the protrusion pipe and configured to generate heat when an electric signal is applied; and a heater fixing portion comprising a bank member protruding in a direction opposite to a direction in which a cigarette is inserted from a surface in contact with the protrusion pipe and an accommodation groove formed to be drawn in the direction in which the cigarette is inserted and accommodating a part of the protrusion pipe and configured to be installed inside the case to support the heater.

The aerosol generation device may further include a sealing member installed in the accommodation groove to seal a gap between the protrusion pipe and the heater fixing portion.

A plurality of accommodation grooves may be formed in the heater fixing portion. One of the plurality of accommodation grooves may accommodate a part of the protrusion pipe, and the sealing member may be installed in another of the plurality of accommodation grooves.

The sealing member may include an elastic material.

According to another exemplary embodiment of the present disclosure, an aerosol generation device includes a case into which a cigarette may be inserted; a protrusion pipe of a hollow shape protruding from one end portion of the case and having an opening; a heater installed at the case such that an end portion is positioned inside the protrusion pipe and configured to generate heat when an electric signal is applied; a heater fixing portion installed inside the case to support the heater, a base portion surrounding and supporting a controller transmitting the electric signal to the heater and installed inside the case to engage with the protrusion pipe; and a sealing member interposed between the protrusion pipe and the base portion to seal a gap between the protrusion pipe and the base portion.

The protrusion pipe may include a sealing groove formed to be drawn in from a surface in contact with the base portion, and the sealing member may be installed in the sealing groove.

The base portion may include a sealing groove formed to be drawn in from a surface in contact with the protrusion pipe, and the sealing member may be installed in the sealing groove.

The sealing member may include an elastic material.

MODE OF DISCLOSURE

With respect to the terms in the various exemplary embodiments, the general terms which are currently and widely used are selected in consideration of functions of structural elements in the various exemplary embodiments of the present disclosure. However, meanings of the terms can be changed according to intention, a judicial precedence, the appearance of a new technology, and the like. In addition, in certain cases, a term which is not commonly used can be selected. In such a case, the meaning of the term will be described in detail at the corresponding portion in the description of the present disclosure. Therefore, the terms used in the various exemplary embodiments of the present disclosure should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and operation and can be implemented by hardware components or software components and combinations thereof.

Hereinafter, the present disclosure will now be described more fully with reference to the accompanying drawings, in which exemplary embodiments of the present disclosure are shown such that one of ordinary skill in the art may easily work the present disclosure. The disclosure may, however, be embodied in many different forms and should not be construed as being limited to the exemplary embodiments set forth herein.

Hereinafter, exemplary embodiments of the present disclosure will be described in detail with reference to the drawings.

FIG. 1 is a drawing illustrating an example in which a cigarette is inserted into an aerosol generation device.

Referring to FIG. 1, the aerosol generation device 1000 may include a battery 1100, a controller 1200, and a heater 1030. Also, the cigarette 2000 may be inserted into an inner space of the aerosol generation device 1000.

FIG. 1 shows the aerosol generation device 1000 with some elements related to the exemplary embodiment. However, it will be understood by one of ordinary skill in the art that other general-purpose components may be further included in the aerosol generation device 1000, in addition to the components illustrated in FIG. 1.

FIG. 1 illustrates that the battery 1100, the controller 1200, and the heater 1030 are arranged in series, but the arrangement of these are not limited thereto. In other words, according to the design of the aerosol generation device 1000, the arrangements of the battery 1100, the controller 1200, and the heater 1030 may be modified.

When the cigarette 2000 is inserted into the aerosol generation device 1000, the aerosol generation device 1000 heats the heater 1030. The temperature of an aerosol generating material in the cigarette 2000 is raised by the heated heater 1030, and thus aerosol is generated. The generated aerosol is delivered to a user through a filter 2200 of the cigarette 2000.

For example, in order to clean an internal space of the aerosol generation device 1000, even when the cigarette 2000 is not inserted into the aerosol generation device 1000, the aerosol generation device 1000 may heat the heater 1030.

The battery 1100 may supply power to be used for the aerosol generation device 1000 to operate. For example, the battery 1100 may supply power for heating the heater 1030 and supply power for operating the controller 1200. Also, the battery 1100 may supply power for operations of a display, a sensor, a motor, etc. mounted in the aerosol generation device 1000.

The controller 1200 may generally control operations of the aerosol generation device 1000. In detail, the controller 1200 controls not only operations of the battery 1100 and the heater, but also operations of other components included in the aerosol generation device 1000. Also, the controller 1200 may check a state of each of the components of the aerosol generation device 1000 to determine whether or not the aerosol generation device 1000 is able to operate.

The controller 1200 may include at least one processor. A processor can be implemented as an array of a plurality of logic gates or can be implemented as a combination of a general-purpose microprocessor and a memory in which a program executable in the microprocessor is stored. It will be understood by one of ordinary skill in the art that the processor can be implemented in other forms of hardware.

The heater 1030 is heated by power supplied from the battery 1100. For example, when the cigarette 2000 is inserted into the aerosol generation device 1000, the heater 1030 may be located inside the cigarette 2000. Thus, the heated heater 1030 may increase a temperature of an aerosol generating material in the cigarette 2000.

The heater 1030 may include an electro-resistive heater. For example, the heater 1030 may include an electrically conductive track, and the heater 1030 may be heated when currents flow through the electrically conductive track. However, the heater 1030 is not limited to the example described above and may be implemented using any other heaters which are capable of being heated to a desired temperature. Here, the desired temperature may be pre-set in the aerosol generation device 1000 or may be manually set by a user.

As another example, the heater 1030 may include an induction heater. In detail, the heater 1030 may include an electrically conductive coil for heating a cigarette by an induction heating method, and the cigarette may include a susceptor which may be heated by the induction heater.

FIG. 1 illustrates that the heater 1030 is inserted into the cigarette 2000, but the position of the heater 1030 is not limited thereto. For example, the heater 1030 may include a tube-type heating element, a plate-type heating element, a needle-type heating element, or a rod-type heating element, and may heat the inside or the outside of the cigarette 2000, according to the shape of the heating element.

Also, the aerosol generation device 1000 may include a plurality of heaters 1030. Here, the plurality of heaters 1030 may be inserted into the cigarette 2000 or may be arranged outside the cigarette 2000. Also, some of the plurality of heaters 1030 may be inserted into the cigarette 2000, and the others may be arranged outside the cigarette 2000. In addition, the shape of the heater 1030 is not limited to the shape illustrated in FIG. 1, and may include various shapes.

The aerosol generation device 1000 may further include general-purpose components in addition to the battery 1100, the controller 1200, and the heater 1030. For example, the aerosol generation device 1000 may include a display capable of outputting visual information and/or a motor for outputting haptic information. Also, the aerosol generation device 1000 may include at least one sensor (a puff detecting sensor, a temperature detecting sensor, a cigarette insertion detecting sensor, etc.).

Also, the aerosol generation device 1000 may be formed to have a structure that allows external air to be introduced or internal air to be discharged even when the cigarette 2000 is inserted into the aerosol generation device 1000.

Although not illustrated in FIG. 1, the aerosol generation device 1000 and an additional cradle may form together a system. For example, the cradle may be used to charge the battery 1100 of the aerosol generation device 1000. Also, the heater 1030 may be heated when the cradle and the aerosol generation device 1000 are coupled to each other.

The cigarette 2000 may be similar to a general combustive cigarette. For example, the cigarette 2000 may be divided into a first portion 2100 including an aerosol generating material and a second portion 2200 including a filter or the like. Alternatively, the second portion 2200 of the cigarette 2000 may also include an aerosol generating material. For example, an aerosol generating material made in the form of granules or capsules may be inserted into the second portion 2200.

The first portion 2100 may be completely inserted into the aerosol generation device 1000, and the second portion 2200 may be exposed to the outside. In some exemplary embodiments, only a portion of the first portion 2100 may be inserted into the aerosol generation device 1000. Otherwise, a portion of the first portion 2100 and a portion of the second portion 2200 may be inserted into the aerosol generation device 1000. The user may puff aerosol while holding the second portion 2200 by the mouth of the user. In this case, the aerosol is generated by the external air passing through the first portion 2100, and the generated aerosol passes through the second portion 2200 and is delivered to the user's mouth.

For example, the external air may flow into at least one air passage formed in the aerosol generation device 1000. For example, opening and closing of the air passage and/or a size of the air passage may be adjusted by the user. Accordingly, the amount of smoke and smoking satisfaction may be adjusted by the user. As another example, the external air may flow into the cigarette 2000 through at least one hole formed in a surface of the cigarette 2000.

Hereinafter, an example of the cigarette 2000 will be described with reference to FIG. 2.

Figure 2:
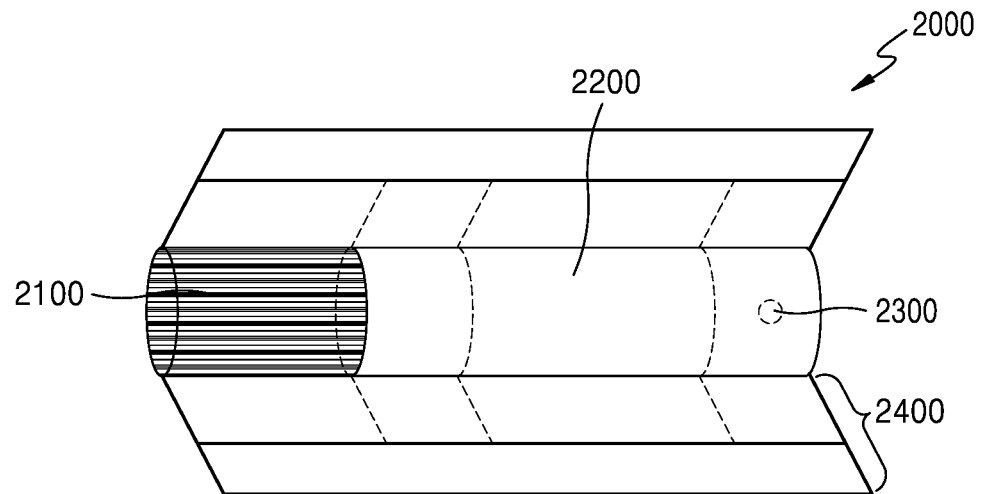
FIG. 2 shows a view showing an example of the cigarette 2000.

FIG. 2 shows a view showing an example of a cigarette.

Referring to FIG. 2, the cigarette 2000 includes a tobacco rod 2100 and a filter rod 2200. The first portion 2100 described above with reference to FIG. 1 includes the tobacco rod 2100, and the second portion 2200 includes the filter rod 2200.

The filter rod 2200 illustrated in FIG. 2 is illustrated as a single segment, but is not limited thereto. In other words, the filter rod 2200 may include a plurality of segments. For example, the filter rod 2200 may include a first segment configured to cool aerosol and a second segment configured to filter a certain component included in the aerosol. Also, as necessary, the filter rod 2200 may further include at least one segment configured to perform other functions.

The cigarette 2000 may be packaged using at least one wrapper 2400. The wrapper 2400 may have at least one hole through which external air may be introduced or internal air may be discharged. For example, the cigarette 2000 may be packaged using one wrapper 2400. As another example, the cigarette 2000 may be doubly packaged using at least two wrappers 2400. For example, the tobacco rod 2100 may be packaged using a first wrapper, and the filter rod 2200 may be packaged using a second wrapper. Also, the tobacco rod 2100 and the filter rod 2200, which are respectively packaged using separate wrappers, may be coupled to each other, and the entire cigarette 2000 may be packaged using a third wrapper. When each of the tobacco rod 2100 and the filter rod 2200 includes a plurality of segments, each segment may be packaged using a separate wrapper. Also, the entire cigarette 2000 including the plurality of segments, which are respectively packaged using the separate wrappers and which are coupled to each other, may be re-packaged using another wrapper.

The tobacco rod 2100 may include an aerosol generating material. For example, the aerosol generating material may include at least one of glycerin, propylene glycol, ethylene glycol, dipropylene glycol, diethylene glycol, triethylene glycol, tetraethylene glycol, and oleyl alcohol, but it is not limited thereto. Also, the tobacco rod 2100 may include other additives, such as flavors, a wetting agent, and/or organic acid. Also, the tobacco rod 2100 may include a flavored liquid, such as menthol or a moisturizer, which is injected to the tobacco rod 2100.

The tobacco rod 2100 may be manufactured in various forms. For example, the tobacco rod 2100 may be formed as a sheet or a strand. Also, the tobacco rod 2100 may be formed as a pipe tobacco, which is formed of tiny bits cut from a tobacco sheet. Also, the tobacco rod 2100 may be surrounded by a heat conductive material. For example, the heat-conducting material may be, but is not limited to, a metal foil such as aluminum foil. For example, the heat conductive material surrounding the tobacco rod 2100 may uniformly distribute heat transmitted to the tobacco rod 2100, and thus, the heat conductivity applied to the tobacco rod may be increased and taste of the tobacco may be improved. Also, the heat conductive material surrounding the tobacco rod 2100 may function as a susceptor heated by the induction heater. Here, although not illustrated in the drawings, the tobacco rod 2100 may further include an additional susceptor, in addition to the heat conductive material surrounding the tobacco rod 2100.

The filter rod 2200 may include a cellulose acetate filter. Shapes of the filter rod 2200 are not limited. For example, the filter rod 2200 may include a cylinder-type rod or a tube-type rod having a hollow inside. Also, the filter rod 2200 may include a recess-type rod. When the filter rod 2200 includes a plurality of segments, at least one of the plurality of segments may have a different shape.

The filter rod 2200 may be formed to generate flavors. For example, a flavoring liquid may be injected onto the filter rod 2200, or an additional fiber coated with a flavoring liquid may be inserted into the filter rod 2200.

Also, the filter rod 2200 may include at least one capsule 2300. Here, the capsule 2300 may generate a flavor or aerosol. For example, the capsule 2300 may have a configuration in which a liquid containing a flavoring material is wrapped with a film. For example, the capsule 2300 may have a spherical or cylindrical shape, but is not limited thereto.

When the filter rod 2200 includes a segment configured to cool the aerosol, the cooling segment may include a polymer material or a biodegradable polymer material. For example, the cooling segment may include pure polylactic acid alone, but the material for forming the cooling segment is not limited thereto. In some exemplary embodiments, the cooling segment may include a cellulose acetate filter having a plurality of holes. However, the cooling segment is not limited to the above-described example and any other cooling segment that is capable of cooling the aerosol may be used.

Figure 3:
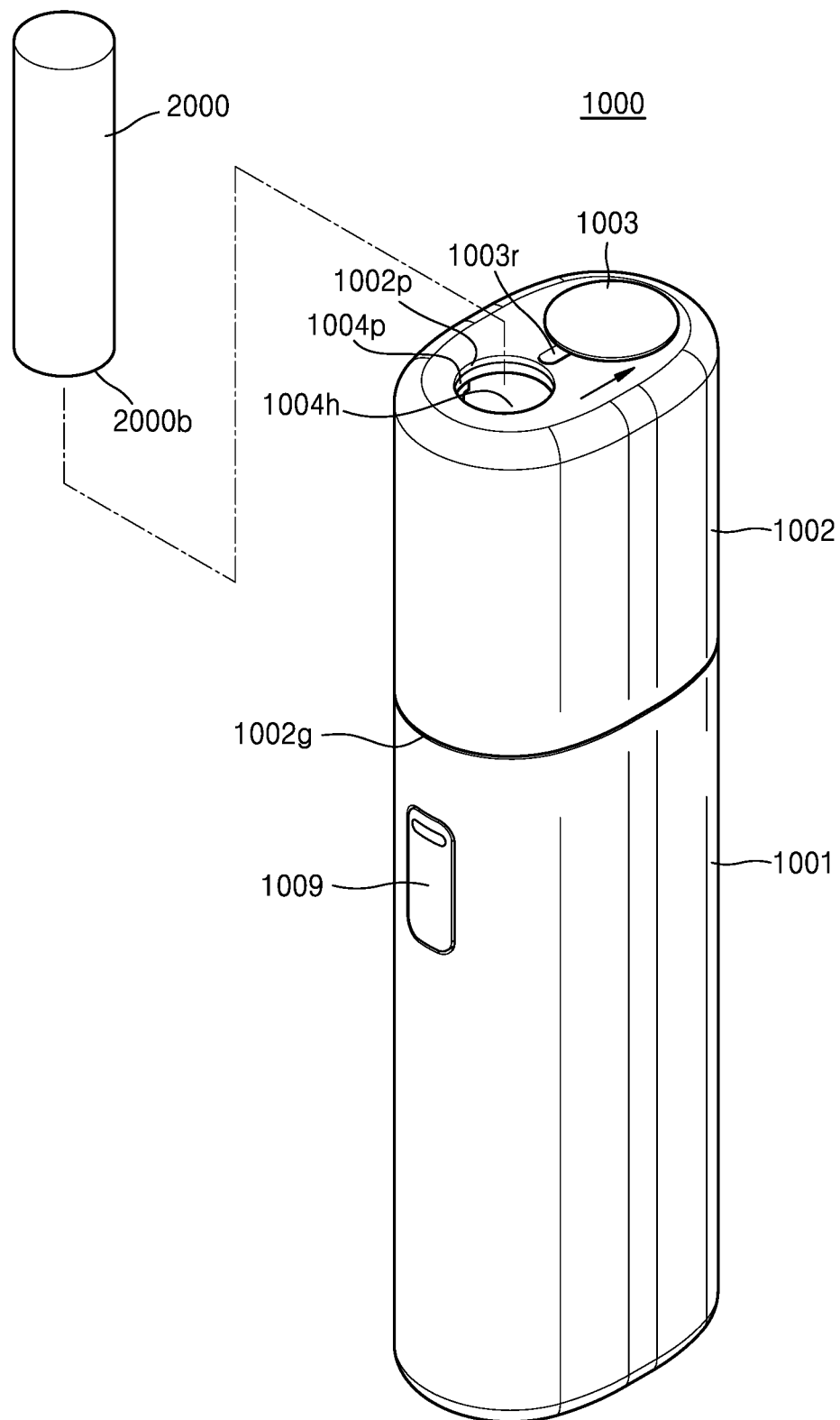
FIG. 3 is a perspective view showing an appearance of an aerosol generation device according to an exemplary embodiment of the present disclosure.

FIG. 3 is a perspective view showing an appearance of an aerosol generation device 1000 according to an exemplary embodiment of the present disclosure.

The aerosol generation device 1000 according to the exemplary embodiment shown in FIG. 3 may include a case 1001 and a cover 1002. Because the cover 1002 is coupled to one end of the case 1001, the case 1001 and the cover 1002 together form the appearance of the aerosol generation device 1000.

The case 1001 forms a part of the appearance of the aerosol generation device 1000 and functions to accommodate and protect various components therein.

The cover 1002 and the case 1001 may be manufactured using a plastic material that does not transfer heat well, or a metallic material coated with a heat blocking material on its surface. The cover 1002 and the case 1001 may be manufactured by, for example, injection molding, 3D printing, or assembling small parts manufactured by injection molding.

A maintaining device (not shown) for maintaining a coupling state of the cover 1002 and the case 1001 may be installed between the cover 1002 and the case 1001. The maintaining device may include, for example, a protrusion and a groove. By maintaining a state in which the protrusion is inserted into the groove, the coupling state of the cover 1002 and the case 1001 may be maintained. The protrusion may be moved by a user pressing an operation button, and separated from the groove.

In addition, the maintaining device may include, for example, a magnet and a metal member that is attracted to the magnet. When the magnet is used in the maintaining device, the magnet may be installed in either the case 1001 or the cover 1002, and the metal member may be installed in the other one. Alternatively, the magnet may be installed in both the case 1001 and the cover 1002.

In the aerosol generation device 1000 according to the exemplary embodiment illustrated in FIG. 3, the cover 1002 is not indispensable, and thus, the cover 1002 may not be installed if necessary.

An outer hole 1002*p* into which a cigarette 2000 may be inserted is formed in an upper surface of the cover 1002 coupled to the case 1001. In addition, a rail 1003*r* is formed at a position adjacent to the outer hole 1002*p* on the upper surface of the cover 1002. The rail 1003*r* is provided with a door 1003 that is slidable along the upper surface of the cover 1002. The door 1003 may slide linearly along the rail 1003*r*.

The door 1003 moves along the rail 1003*r* in the direction of an arrow in FIG. 3, such that the door 1003 serves to expose, to the outside, the outer hole 1002*p* and an insertion hole 1004*p* that allow the cigarette 2000 to pass through the cover 1002 and be inserted into the case 1001. The outer hole 1002*p* of the cover 1002 serves to expose, to the outside, the insertion hole 1004*p* of an accommodation passage 1004*h* that may accommodate the cigarette 2000.

When the outer hole 1002*p* is exposed to the outside by the door 1003, the user may insert an end portion 2000*b* of the cigarette 2000 into the outer hole 1002*p* and the insertion hole 1004*p* to mount the cigarette 2000 in the accommodation passage 1004*h* formed inside the cover 1002.

In the exemplary embodiment shown in FIG. 3, the door 1003 may move linearly with respect to the cover 1002. However, the exemplary embodiment is not limited by the coupling structure of the door 1003 and the cover 1002. For example, the door 1003 may be rotatably installed on the cover 1002 via a hinge assembly. When the hinge assembly is used, the door 1003 may rotate to the side of the outer hole 1002*p* along the extension of the upper surface of the cover 1002, or the door 1003 may rotate away from the upper surface of the cover 1002.

The rail 1003*r* has a concave groove shape, but the exemplary embodiment is not limited by the shape of the rail 1003*r*. For example, the rail 1003*r* may have a convex shape and may extend in a curved shape rather than a straight shape.

A button 1009 is installed in the case 1001. An operation of the aerosol generation device 1000 may be controlled in accordance with the operation of the button 1009.

In a state where the cover 1002 is coupled to the case 1001, an outer air inflow gap 1002*g* that allows air to flow into the inside of the cover 1002 is formed at a portion where the cover 1002 and the case 1001 are coupled to each other.

Figure 4:
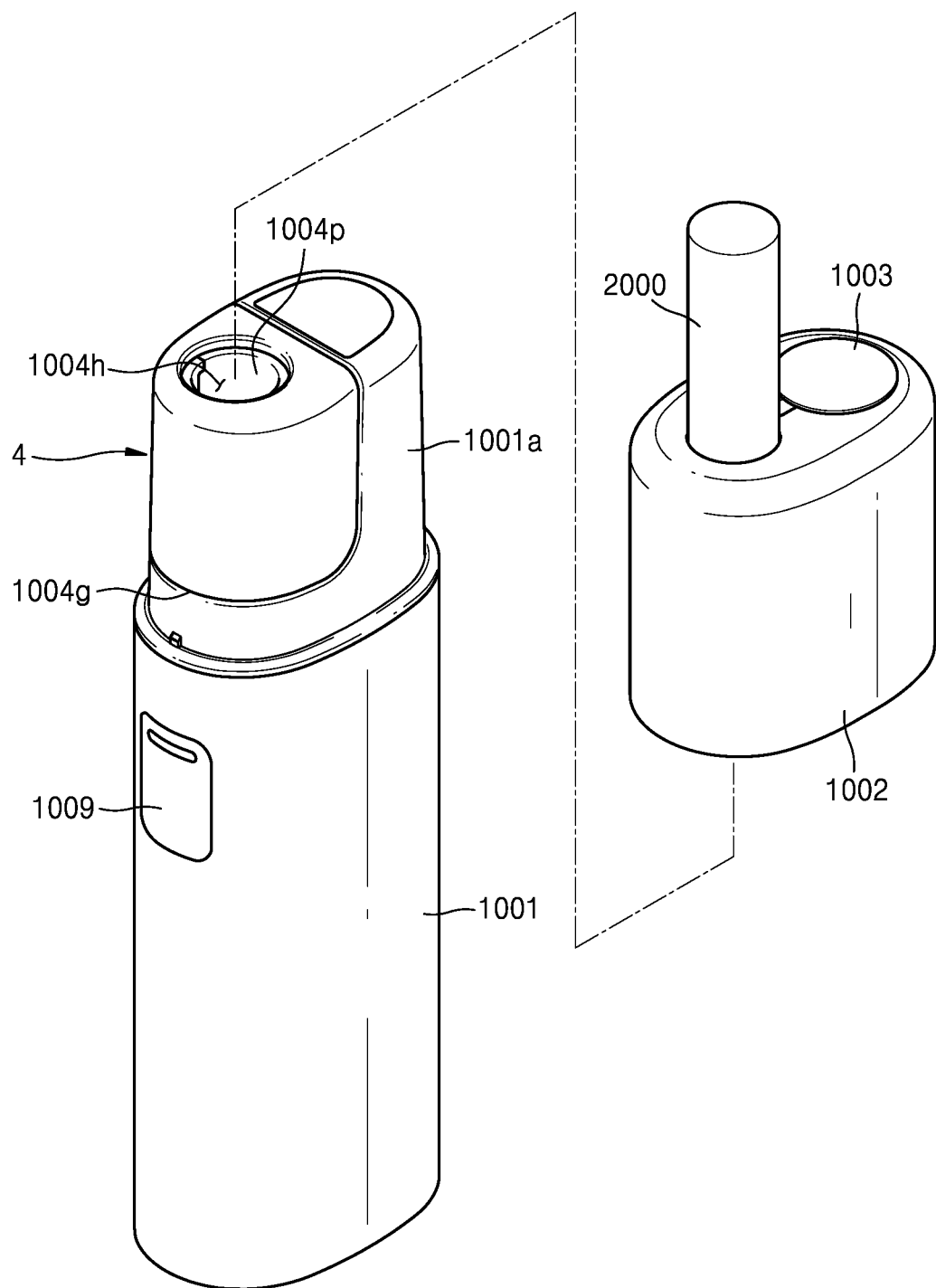
FIG. 4 is a perspective view illustrating an operation state in which some components have been separated in the aerosol generation device according to the exemplary embodiment shown in FIG. 3.
Figure 5:
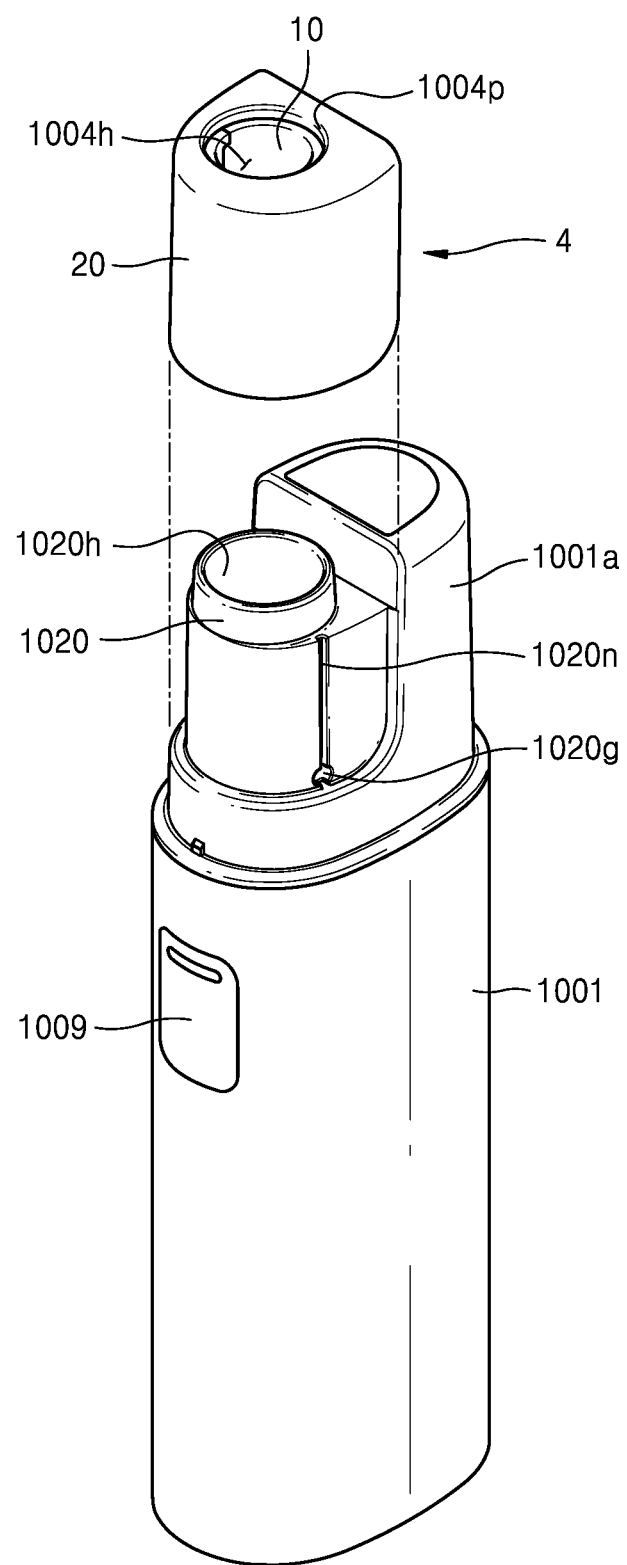
FIG. 5 is a perspective view illustrating an operation state in which some components are separated in the aerosol generation device according to the exemplary embodiment shown in FIG. 3.
Figure 6:
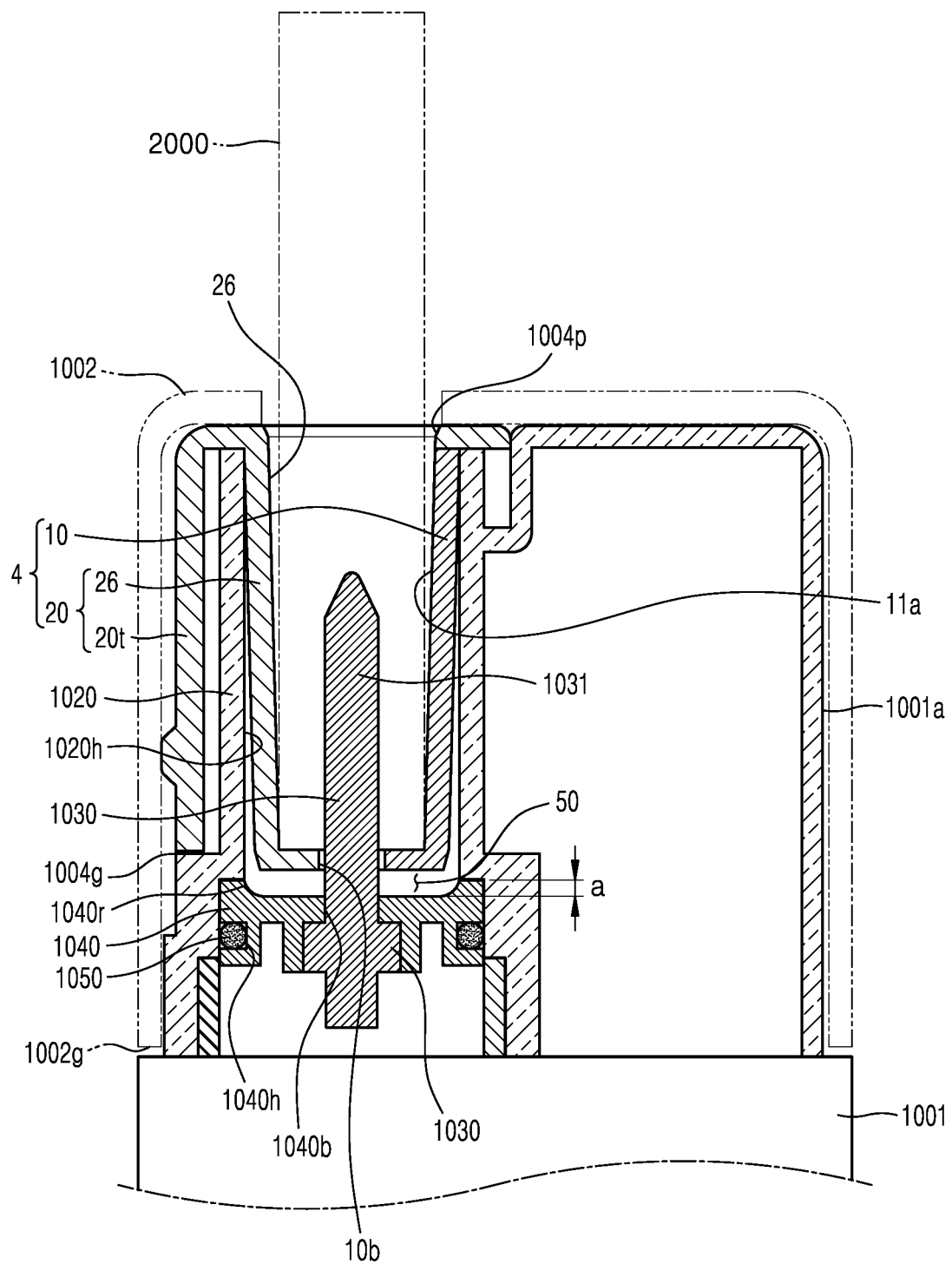
FIG. 6 is a side cross-sectional view showing some components of the aerosol generation device according to the exemplary embodiment shown in FIG. 3.

FIG. 4 is a perspective view illustrating an operation state in which some components have been separated in the aerosol generation device 1000 according to the exemplary embodiment shown in FIG. 3. FIG. 5 is a perspective view illustrating an operation state in which some components are being separated in the aerosol generation device 1000 according to the exemplary embodiment shown in FIG. 3. FIG. 6 is a side cross-sectional view showing some components of the aerosol generation device 1000 according to the exemplary embodiment shown in FIG. 3.

As illustrated in FIG. 4, in a state where the cigarette 2000 is inserted into the aerosol generation device 1000, a user may inhale aerosol from the cigarette 2000.

When the use of the cigarette 2000 ends, the user may perform a cleaning operation of removing a tobacco material remaining in the aerosol generation device 1000 after separating the cigarette 2000 from the aerosol generation device 1000.

The user may perform the cleaning operation of the aerosol generation device 1000 by separating the cover 1002 from the case 1001 of the aerosol generation device 1000, separating a cigarette support portion 4 from the case 1001, exposing an internal space of the aerosol generation device 1000 and a heater 1030 to the outside, and removing the tobacco material.

Referring to FIG. 4, the cover 1002 may be coupled to one end portion 1001*a* of the case 1001 to cover the cigarette support portion 4 coupled to the one end portion 1001*a* of the case 1001. In addition, the cover 1002 may be separated from the case 1001 as necessary.

When removing the cigarette 2000 from the aerosol generation device 1000 after the use of the cigarette 2000, the user may pull out the cigarette 2000 from the case 1001 while rotating the cigarette 2000 by hand.

Alternatively, as shown in FIG. 4, if the user rotates the cigarette 2000 and then pulls the cover 1002, the cover 1002 may be separated from the case 1001 together with the cigarette 2000.

By separating the cigarette 2000 from the case 1001 while rotating the cigarette 2000, the cigarette 2000 may be released from the heater 1030, and at the same time, a tobacco material attached to the cigarette 2000 may be discharged to the outside of the case 1001 together with the cigarette 2000.

In case of pulling the cover 1002 without rotating the cigarette 2000, the cigarette 2000 is separated from the case 1001, but a part of the cigarette 2000, for example, a tobacco part, may not be discharged from the case 1001 and may remain on the heater 1030. In this case, the user may separate the cigarette support portion 4 from the case 1001 as shown in FIG. 5 after removing the cover 1002 from the case 1001. At this time, the tobacco part remaining on the heater 1030 is separated from the case 1001 together with the cigarette support portion 4. Thereafter, the user may remove the tobacco part remaining on the separated cigarette support portion 4.

Referring to FIGS. 5 and 6, the aerosol generation device 1000 includes the case 1001 into which the cigarette 2000 may be inserted, a protrusion pipe 1020 of a hollow shape protruding from the one end portion 1001*a* of the case 1001 and open toward the outside, the heater 1030 installed in the case 1001 such that an end portion 1031 is positioned inside the protrusion pipe 1020 and generating heat when an electric signal is applied, and a heater fixing portion 1040 including a round surface 1040*r* extending from an inner surface of the protrusion pipe 1020 and installed inside the protrusion pipe 1020 to support the heater 1030. In addition, the aerosol generation device 1000 further includes the cigarette support portion 4 which may be coupled to and separated from the protrusion pipe 1020.

As shown in FIG. 5, when the user pulls upward the cigarette support portion 4 by hand in a state where the cigarette support portion 4 is coupled to the case 1001, the cigarette support portion 4 may be separated from the case 1001.

Referring to FIG. 6, the protrusion pipe 1020 surrounds and protects the heater 1030. The protrusion pipe 1020 supports the cigarette supporting portion 4 when the cigarette supporting portion 4 is coupled to the protrusion pipe 1020.

Due to the hollow shape of the protrusion pipe 1020, the protrusion pipe 1020 includes a coupling passage 1020*h* into which at least a part of the cigarette support portion 4 may be inserted. The upper end of the coupling passage 1020*h* opens to the outside toward the upper direction of the aerosol generation device 1000.

The heater 1030 that performs a function of heating the cigarette 2000 is installed in the case 1001. The heater 1030 is installed in the case 1001 such that the upper end portion 1031 is positioned inside the protrusion pipe 1020. When the cigarette 2000 is accommodated in the cigarette support portion 4 while the cigarette support portion 4 is coupled to the protrusion pipe 1020, the upper end 1031 of the heater 1030 is inserted into the bottom surface of the end portion 2000*b* of the cigarette 2000.

The heater 1030 is electrically connected to the battery (1100 of FIG. 1) and the controller (1200 of FIG. 1) installed in the case 1001. When electricity is supplied to the heater 1030 while the cigarette 2000 is inserted into the end portion 1031 of the heater 1030, the heater 1030 is heated and thus the cigarette 2000 is heated.

Referring to FIG. 5, the cigarette support portion 4 may be inserted into the coupling passage 1020*h* inside the protrusion pipe 1020 through an opening of the protrusion pipe 1020. The cigarette support portion 4 includes an inner cylinder 10 inserted into the protrusion pipe 1020 and an outer cylinder 20 supporting the inner cylinder 10.

Referring to FIG. 6, the outer cylinder 20 of the cigarette support portion 4 includes an extension support surface 26 protruding inward from an outer wall 20*t* having an approximately semi-cylindrical shape, and the extension support surface 26 is spaced apart from the outer wall 20*t*. When the cigarette support portion 4 is coupled to the protrusion pipe 1020, the protrusion pipe 1020 is inserted between the outer wall 20*t* and the extension support surface 26 such that a coupling state of the cigarette support portion 4 and the protrusion pipe 1020 may be stably maintained.

According to the stable coupling structure of the cigarette support portion 4 and the protrusion pipe 1020 as described above, even if external force is applied to the aerosol generation device 1000 due to an impact, separation or damage of the components of the aerosol generation device 1000 may be reduced. As a result, good durability and stability may be ensured even when the aerosol generation device 1000 is used for a long time.

In addition, because the cigarette support portion 4 may be easily separated from the case 1001, the cleaning operation may be performed surely and conveniently.

In addition, the protrusion pipe 1020 may perform a function of directly supplying the outside air to an end of the cigarette 2000. Referring to FIG. 5, the protrusion pipe 1020 includes an air hole 1020g connecting the inside and the outside of the protrusion pipe 1020, and an air flow path 1020n extending along a surface of the protrusion pipe 1020 to guide the flow of air to the air hole 1020g.

A plurality of air holes 1020g may be formed spaced apart along the circumferential direction of the protrusion pipe 1020. The air hole 1020g and the air flow path 1020n form a flow passage of air for allowing air outside the protrusion pipe 1020 to flow into the protrusion pipe 1020.

Referring to FIG. 6, when the cigarette support portion 4 is coupled to the protrusion pipe 1020, the extension support surface 26 of the cigarette support portion 4 is inserted into the protrusion pipe 1020. While the extension support surface 26 of the cigarette support portion 4 moves downward along the protrusion pipe 1020, the heater 1030 positioned inside the protrusion pipe 1020 passes through a heater insertion hole 10b of the cigarette support portion 4.

In the state where the cigarette support portion 4 is coupled to the protrusion pipe 1020, the end portion 1031 of the heater 1030 passes through the heater insertion hole 10b of the cigarette support portion 4 and is positioned inside the cigarette support portion 4. Accordingly, when the cigarette 2000 is accommodated in the cigarette support portion 4 in the state where the cigarette support portion 4 is coupled to the protrusion pipe 1020, the end portion 1031 of the heater 1030 is inserted into the cigarette 2000.

When the user of the aerosol generation device 1000 inserts the cigarette 2000 into the accommodation passage 1004h, the cigarette 2000 moves along the cigarette support portion 4. When the end portion 2000b of the cigarette 2000 reaches the bottom of the cigarette support portion 4, a feeling of contact between the bottom of the cigarette support portion 4 and the end portion 2000b of the cigarette 2000 is delivered to a user's hand holding the cigarette 2000. Therefore, the user may conveniently mount the cigarette 2000 to the aerosol generation device 1000 by pushing the cigarette 2000 into the aerosol generation device 1000.

When the user separates the cigarette 2000 from the cigarette support portion 4, the user may pull the cigarette 2000 out of the cigarette support portion 4 while rotating the cigarette 2000 by hand. While the user rotates the cigarette 2000 by hand, the cigarette 2000 and the heater 1030 attached to each other by a tobacco material may be completely separated.

After separating the cigarette 2000 from the cigarette support portion 4, the user may perform the cleaning operation on the inside of the cigarette support portion 4. When the user separates the cigarette support portion 4 from the case 1001 in order to perform the cleaning operation, the user may pull out the cigarette support portion 4 to the outside of the case 1001 by holding the cigarette support portion 4 by hand.

The heater fixing portion 1040 may be installed inside the protrusion pipe 1020 and include the through hole 1040b through which the end portion 1031 of the heater 1030 may pass. The heater fixing portion 1040 may be installed inside the case 1001 and surrounded by the protrusion pipe 1020. Because the protrusion pipe 1020 and the heater fixing portion 1040 are distinct components, a gap of a predetermined interval may be formed between the protrusion pipe 1020 and the heater fixing portion 1040.

Meanwhile, the upper end portion 1031 of the heater 1030 protrudes upward through the through hole 1040b of the heater fixing portion 1040, and also passes through the heater insertion hole 10b of the protrusion pipe 1020 such that the upper end portion 1031 of the heater 1030 is positioned inside the cigarette support portion 4.

The area of the heater insertion hole 10b may be formed to be larger than the cross-sectional area of the heater 1030 penetrating the heater insertion hole 10b. According to this structure, the outside air may enter and exit through the heater insertion hole 10b.

An inner space 50 is formed between the protrusion pipe 1020 and the cigarette support portion 4 and between the heater fixing portion 1040 and the cigarette support portion 4. One side of the inner space 50 is connected to an inflow passage 1004g through which the outside air flows when the cigarette support portion 4 is mounted to the protrusion pipe 1020, and the other side is connected to the heater insertion hole 10b.

According to this structure, the outside air flown into the inflow passage 1004g flows into the inner space 50 along the gap between the cigarette support portions 4 and the protrusion pipe 1020, and may be inhaled by the user in the inner space 50 according to an inhalation operation of the user through the heater insert hole 10b via the cigarette 2000.

That is, the inside of the cigarette support portion 4 into which the cigarette 2000 is inserted and the inner space 50 may be connected to each other through a minute gap formed between the heater 1030 and the heater insertion hole 10b. At this time, the cigarette 2000 is heated to generate an aerosol, but at the same time, the aerosol may also be liquefied to form a liquid material at the end portion 2000b of the cigarette 2000 and leaked toward the inner space 50 through the gap formed between the heater 1030 and the heater insertion hole 10b. In addition, the aerosol remaining in the inner space 50 may be liquefied and formed on the inner wall surface of the protrusion pipe 1020, and may flow down along the inner wall surface of the protrusion pipe 1020. Herein, the term "liquid material" may refer to water or an aerosol material included in a tobacco sheet medium of the cigarette 2000.

If the liquid material remaining in the inner space 50 flows into the gap formed between the protrusion pipe 1020 and the cigarette support portion 4, the liquid material may penetrate into the aerosol generation device 1000 along the inner wall surface of the protrusion pipe 1020. If the liquid material penetrated therein wets the battery (1100 of FIG. 1) or the controller (1200 of FIG. 1) which transmits an electric signal to the heater 1030, the battery 1100 or the controller 120 may be damaged.

In order to solve this problem, the round surface 1040r of the heater fixing portion 1040 may serve as a kind of breakwater that collects liquid materials so as to prevent the liquid material flowing into the inner space 50 from penetrating into the aerosol generation device 1000 through the gap between the protrusion pipe 1020 and the heater fixing portion 1040.

In addition, the round surface 1040r may assist the liquid material generated in the inner space 50 to be delivered to the heater 1030 without being fixed to edges of the inner space 50. For example, the liquid material delivered to the heater 1030 by the round surface 1040r may be heated by the heater 1030 and aerosolized again.

In addition, the aerosol generation device 1000 may further include a sealing member 1050 interposed between the protrusion pipe 1020 and the heater fixing portion 1040 to seal the gap between the protrusion pipe 1020 and the heater fixing portion 1040.

The heater fixing portion 1040 may further include a sealing groove 1040h formed to be drawn in from a surface in contact with the protrusion pipe 1020, and the sealing member 1050 may be installed in the sealing groove 1040h. However, the exemplary embodiment is not limited thereto, and the sealing member 1050 may be installed in a sealing groove (not shown) formed in the protrusion pipe 1020.

The exemplary embodiment shown in the drawings depicts the case in which the sealing member 1050 is circular, but the exemplary embodiment is not limited thereto. The sealing member 1050 may include an elastic material, and is not limited to a specific shape as long as it is capable of sealing the gap between the protrusion pipe 1020 and the heater fixing portion 1040 in order to prevent the liquid material from penetrating into the aerosol generation device 1000 through the gap formed between the protrusion pipe 1020 and the heater fixing portion 1040.

Even when the liquid material is accumulated in the inner space 50 higher than the height a of the round surface 1040r of the heater fixing portion 1040 and flows down along the gap formed between the protrusion pipe 1020 and the heater fixing portion 1040, the sealing member 1050 may protect the battery 1100 and the controller 1200 installed therein by preventing the liquid material from penetrating inside the aerosol generation device 1000.

Figure 7:
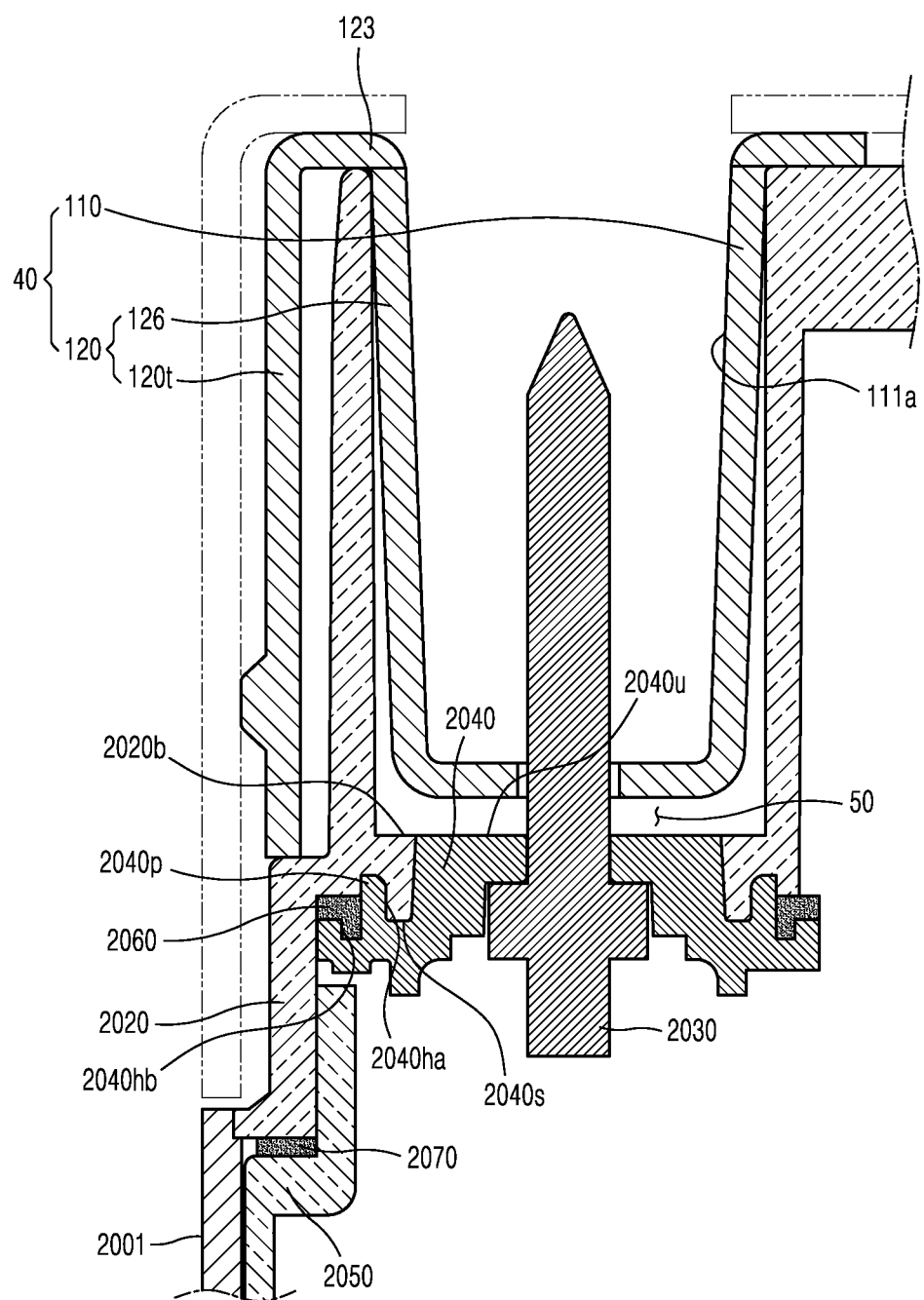
FIG. 7 is a side cross-sectional view showing some components of an aerosol generation device according to another exemplary embodiment of the present disclosure.

FIG. 7 is a side cross-sectional view showing some components of the aerosol generation device 1000 according to another exemplary embodiment of the present disclosure.

In the exemplary embodiment of the aerosol generation device 1000 shown in FIG. 7, other than the structure of a heater fixing portion 2040, the installation positions of sealing members 2060 and 2070 and the coupling structure of a base portion 2050 that will be described later, most components are the same as those described with reference to FIG. 6, and thus detailed descriptions thereof will be omitted.

First, the heater fixing portion 2040 illustrated in FIG. 7 will be described. The heater fixing portion 2040 includes a bank member 2040p installed inside a protrusion pipe 2020 to support the heater 2030 and protruding upward from a sunken surface 2040s in contact with the protrusion pipe 2020, and accommodation grooves 2040ha and 2040hb formed to be drawn in from the surface in contact with the protrusion pipe 2020 to accommodate a part of the protrusion pipe 2020.

Here, the term 'upward' means not only an accurate vertical direction in which the bank member 2040p shown in the figure protrudes, but also a direction intersecting with a horizontal direction. That is, the bank member 2040p may protrude in the vertical direction as shown in the figure, but is not limited thereto. For example, the bank member 2040p may also protrude upward in an inclined direction.

According to this structure, even if a liquid material accumulated in the inner space 50 flows into a gap between the inner bottom surface 2020b of the protrusion pipe 2020 and the upper surface 2040u of the heater fixing portion 2040, the penetration of the liquid material into the aerosol generation device 1000 may be primarily prevented by the bank member 2040p because the leakage is collected on the sunken surface 2040s. In addition, since the sealing member 2060 is installed in the accommodation groove 2040hb to seal the gap between the protrusion pipe 2020 and the heater fixing portion 2040, the penetration of the liquid material into the aerosol generation device 1000 may be secondarily prevented by the sealing member 2060.

According to FIG. 7, the heater fixing portion 2040 according to an exemplary embodiment is depicted as including the two accommodation grooves 2040ha and 2040hb, but the exemplary embodiment is not limited thereto and the heater fixing portion 2040 may include one or more accommodation grooves.

As an example, referring to FIG. 7, a part of the protrusion pipe 2020 may be accommodated in the accommodation groove 2040ha adjacent to the heater 2030, and the sealing member 2060 may be installed in the accommodation groove 2040hb far from the heater 2030. However, the reverse structure may be adopted. Further, the sealing member 2060 may be installed in both the accommodation grooves 2040ha and 2040hb.

Meanwhile, the aerosol generation device 1000 according to the exemplary embodiment shown in FIG. 7 may further include the base portion 2050 and the sealing member 2070. The base portion 2050 may surround and support the battery (1100 of FIG. 1) and the controller (1200 of FIG. 2), which transmit an electrical signal to the heater 2030. The base portion 2050 may be installed in the case 2001 to engage with the protrusion pipe 2020. The sealing member 2070 may be interposed between the protrusion pipe 2020 and the base portion 2050 to seal a gap between the protrusion pipe 2020 and the base portion 2050.

The sealing member 2070 may be installed in a sealing groove (not shown) formed in the protrusion pipe 2020 or the base portion 2050 like the sealing groove 1040h of the heater fixing portion 1040 shown in FIG. 6, but the exemplary embodiment is not limited thereto. As another example, a sealing groove may not be formed in the protrusion pipe 2020 or the base portion 2050 of FIG. 7. Instead, the sealing member 2070 may be interposed between the protrusion pipe 2020 and the base portion 2050 in a compressed state.

That is, like the sealing member 1050 shown in FIG. 6, the sealing members 2060 and 2070 shown in FIG. 7 may also include an elastic material. That is, the sealing members 2060 and 2070 may seal the gap between the protrusion pipe 2020 and the heater fixing portion 2040 and between the protrusion pipe 2020 and the base portion 2050 thereby preventing the liquid material from penetrating into the aerosol generation device 1000.

The configuration and effect of the exemplary embodiments described above are provided for illustrative purposes only and it will be understood by those of ordinary skill in the art that various changes and modifications are made therein. Therefore, the true scope of the present disclosure should by defined by the appended claims.

INDUSTRIAL APPLICABILITY

According to the exemplary embodiments of the present disclosure as described above, it is possible to prevent the liquid material from penetrating into the aerosol generation device.

What is claimed is:
1. An aerosol generation device comprising:
a case into which a cigarette is to be inserted;
a protrusion pipe protruding from one end portion of the case and having a cavity for receiving the cigarette;
a heater installed in the case such that an end portion of the heater is positioned in the cavity, and configured to generate heat; and a heater fixing portion installed inside the protrusion pipe and configured to fix a position of the heater with respect to the protrusion pipe, wherein an edge of an upper surface of the heater fixing portion is curvedly raised and meets an inner side surface of the protrusion pipe.

2. The aerosol generation device of claim 1, further comprising a sealing member interposed between the protrusion pipe and the heater fixing portion to seal a gap between the protrusion pipe and the heater fixing portion.

3. The aerosol generation device of claim 2, wherein
the heater fixing portion further comprises a sealing groove formed in a surface in contact with the protrusion pipe, and
wherein the sealing member is installed in the sealing groove.

4. The aerosol generation device of claim 2, wherein
the protrusion pipe comprises a sealing groove formed in a surface in contact with the heater fixing portion, and
wherein the sealing member is installed in the sealing groove.

5. The aerosol generation device of claim 2, wherein the sealing member comprises an elastic material.

6. An aerosol generation device comprising:
a case into which a cigarette is to be inserted;
a protrusion pipe protruding from one end portion of the case and having a cavity for receiving the cigarette;
a heater installed in the case such that an end portion of the heater is positioned in the cavity, and configured to generate heat; and
a heater fixing portion installed inside the protrusion pipe, configured to fix a position of the heater with respect to the protrusion pipe,
wherein an upper surface of the heater fixing portion meets an inner bottom surface of the protrusion pipe, thereby defining a bottom of the cavity, and
wherein the heater fixing portion comprises a sunken surface positioned lower than the upper surface and formed between a wall extending downward from the upper surface and a bank member protruding upward from an outer edge of the sunken surface, such that liquid leaking between the upper surface of the heater fixing portion and the inner bottom surface of the protrusion pipe is collected on the sunken surface.

7. The aerosol generation device of claim 6, wherein
the heater fixing portion comprises an accommodation groove formed to be drawn in from a surface in contact with the protrusion pipe to accommodate a part of the protrusion pipe, and wherein a sealing member is installed in the accommodation groove to seal a gap between the protrusion pipe and the heater fixing portion.

8. The aerosol generation device of claim 7, wherein
a plurality of accommodation grooves including the accommodation groove are formed in the heater fixing portion,
one of the plurality of accommodation grooves accommodates a part of the protrusion pipe, and
the sealing member is installed in another of the plurality of accommodation grooves.

9. The aerosol generation device of claim 7, wherein the sealing member comprises an elastic material.

10. An aerosol generation device comprising:
a case into which a cigarette is to be inserted;
a protrusion pipe protruding upward from one end portion of the case and having a cavity for receiving the cigarette;
a heater installed in the case such that an end portion of the heater is positioned in the cavity, and configured to generate heat;
a heater fixing portion installed inside the case and configured to fix a position of the heater with respect to the protrusion pipe;
a base portion surrounding and supporting a battery and a controller, which control operation of the heater, and installed inside the case to be engaged with the protrusion pipe; and
a sealing member interposed between the protrusion pipe and the base portion to seal a gap between the protrusion pipe and the base portion.

11. The aerosol generation device of claim 10, wherein
the protrusion pipe comprises a sealing groove formed to be drawn in from a surface in contact with the base portion, and
wherein the sealing member is installed in the sealing groove.

12. The aerosol generation device of claim 10, wherein
the base portion comprises a sealing groove formed to be drawn in from a surface in contact with the protrusion pipe, and
wherein the sealing member is installed in the sealing groove.

13. The aerosol generation device of claim 10, wherein the sealing member comprises an elastic material.

\* \* \* \* \*